(12) United States Patent
Chou et al.

(10) Patent No.: US 8,978,444 B2
(45) Date of Patent: Mar. 17, 2015

(54) GAS ANALYTE SPECTRUM SHARPENING AND SEPARATION WITH MULTI-DIMENSIONAL MICRO-GC FOR GAS CHROMATOGRAPHY ANALYSIS

(75) Inventors: Tsung-Kuan A. Chou, San Jose, CA (US); Shih-Chi Chu, Taipei (TW); Chia-Sheng Cheng, Sihu shiang (TW); Li-Peng Wang, San Jose, CA (US); Chien-Lin Huang, Sinjhuang (TW)

(73) Assignee: Tricorn Tech Corporation, San Jose, CA (US)

( * ) Notice: Subject to any disclaimer, the term of this patent is extended or adjusted under 35 U.S.C. 154(b) by 824 days.

(21) Appl. No.: 13/089,850

(22) Filed: Apr. 19, 2011

(65) Prior Publication Data

US 2011/0259081 A1    Oct. 27, 2011

Related U.S. Application Data

(60) Provisional application No. 61/327,392, filed on Apr. 23, 2010.

(51) Int. Cl.
*G01N 30/02* (2006.01)
*G01N 30/30* (2006.01)
(Continued)

(52) U.S. Cl.
CPC .............. *G01N 30/30* (2013.01); *G01N 29/022* (2013.01); *G01N 30/463* (2013.01); *G01N 30/465* (2013.01); *G01N 30/6095* (2013.01); *G01N 30/468* (2013.01); *G01N 2030/884* (2013.01); *G01N 2291/021* (2013.01);
(Continued)

(58) Field of Classification Search
CPC . G01N 29/022; G01N 303/30; G01N 30/463; G01N 30/465; G01N 30/468; G01N 30/6095; G01N 2030/122; G01N 2030/884; G01N 2291/021; G01N 2291/0256; G01N 2291/0423; G01N 2291/0426
USPC .............................................. 73/23.35, 23.42
See application file for complete search history.

(56) References Cited

U.S. PATENT DOCUMENTS

| 4,470,298 A | 9/1984 | Jibelian |
| 4,869,876 A | 9/1989 | Arfman et al. |

(Continued)

FOREIGN PATENT DOCUMENTS

| CN | 2192933 | 3/1995 |
| CN | 2439025 | 7/2001 |

(Continued)

OTHER PUBLICATIONS

U.S. Appl. No. 13/332,064—Non-Final Office Action, mailed Jun. 7, 2013, 23 pages.

(Continued)

*Primary Examiner* — Daniel S Larkin
(74) *Attorney, Agent, or Firm* — Blakely Sokoloff Taylor & Zafman LLP

(57) ABSTRACT

The disclosure describes embodiments of an apparatus including a first gas chromatograph including a fluid inlet, a fluid outlet, and a first temperature control. A controller is coupled to the first temperature control and includes logic to apply a first temperature profile to the first temperature control to heat, cool, or both heat and cool the first gas chromatograph. Other embodiments are disclosed and claimed.

22 Claims, 20 Drawing Sheets

US 8,978,444 B2

Page 2

(51) Int. Cl.
*G01N 29/02* (2006.01)
*G01N 30/46* (2006.01)
*G01N 30/60* (2006.01)
*G01N 30/88* (2006.01)

(52) U.S. Cl.
CPC ............... *G01N 2291/0256* (2013.01); *G01N 2291/0423* (2013.01); *G01N 2291/0426* (2013.01)
USPC ...................................................... 73/23.42

(56) References Cited

U.S. PATENT DOCUMENTS

| | | | |
|---|---|---|---|
| 4,888,295 A | 12/1989 | Zaromb et al. | |
| 5,092,155 A | 3/1992 | Rounbehler et al. | |
| 5,108,468 A | 4/1992 | Ligon, Jr. | |
| 5,108,705 A | 4/1992 | Rounbehler et al. | |
| 5,109,691 A | 5/1992 | Corrigan et al. | |
| 5,152,176 A * | 10/1992 | Bryselbout et al. | 73/23.41 |
| 5,471,055 A | 11/1995 | Costanzo et al. | |
| 5,492,555 A * | 2/1996 | Strunk et al. | 95/86 |
| 5,611,846 A | 3/1997 | Overton et al. | |
| 6,306,200 B1 | 10/2001 | Yu | |
| 6,497,138 B1 | 12/2002 | Abdel-Rahman et al. | |
| 6,828,910 B2 | 12/2004 | VanRyzin et al. | |
| 6,914,220 B2 | 7/2005 | Tian et al. | |
| 7,153,272 B2 | 12/2006 | Talton | |
| 7,343,779 B1 | 3/2008 | Yu | |
| 7,437,779 B2 | 10/2008 | Kenny et al. | |
| 7,926,368 B2 | 4/2011 | Ryan | |
| 8,087,283 B2 | 1/2012 | Wang et al. | |
| 8,104,513 B2 * | 1/2012 | Furukawa | 137/806 |
| 8,277,544 B2 * | 10/2012 | Guan et al. | 96/101 |
| 8,613,215 B2 * | 12/2013 | Lambertus et al. | 73/23.42 |
| 2002/0148353 A1 * | 10/2002 | Seeley | 95/86 |
| 2003/0015019 A1 | 1/2003 | O'Brien | |
| 2003/0233862 A1 | 12/2003 | Wise et al. | |
| 2004/0236244 A1 | 11/2004 | Allen et al. | |
| 2005/0063865 A1 | 3/2005 | Bonne et al. | |
| 2005/0065446 A1 | 3/2005 | Talton | |
| 2005/0085740 A1 | 4/2005 | Davis et al. | |
| 2005/0264926 A1 | 12/2005 | Burts-Cooper et al. | |
| 2005/0277200 A1 * | 12/2005 | Cal et al. | 436/161 |
| 2006/0038402 A1 * | 2/2006 | Norman et al. | 285/384 |
| 2006/0046749 A1 | 3/2006 | Pomerantz et al. | |
| 2006/0222568 A1 | 10/2006 | Wang et al. | |
| 2007/0000305 A1 | 1/2007 | Ma et al. | |
| 2007/0000838 A1 | 1/2007 | Shih et al. | |
| 2007/0062255 A1 | 3/2007 | Talton | |
| 2007/0193336 A1 * | 8/2007 | McCurry et al. | 73/23.42 |
| 2007/0256474 A1 | 11/2007 | Paakkanen et al. | |
| 2008/0092626 A1 | 4/2008 | Lehmann | |
| 2008/0121016 A1 | 5/2008 | Shah et al. | |
| 2008/0233636 A1 | 9/2008 | Ryan | |
| 2008/0264491 A1 | 10/2008 | Klee et al. | |
| 2008/0300501 A1 | 12/2008 | Willard et al. | |
| 2009/0126457 A1 * | 5/2009 | Fisher | 73/23.42 |
| 2009/0308136 A1 | 12/2009 | Wang et al. | |
| 2010/0000291 A1 * | 1/2010 | White | 73/23.41 |
| 2011/0005300 A1 | 1/2011 | Wang et al. | |
| 2011/0023581 A1 | 2/2011 | Chou et al. | |
| 2011/0252873 A1 * | 10/2011 | Vorm | 73/61.53 |
| 2012/0090378 A1 | 4/2012 | Wang et al. | |

FOREIGN PATENT DOCUMENTS

| | | |
|---|---|---|
| CN | 2520508 | 11/2002 |
| CN | 1584589 A | 2/2005 |
| CN | 2798088 | 7/2006 |
| CN | 2859526 | 1/2007 |
| CN | 1954208 A | 4/2007 |
| CN | 1979172 A | 6/2007 |
| CN | 101196457 A | 6/2008 |
| CN | 201133905 Y | 10/2008 |
| DE | 196 01 571 A1 | 7/1997 |
| EP | 0 573 060 A2 | 12/1993 |
| EP | 0 574 027 A2 | 12/1993 |
| EP | 0 654 667 A1 | 5/1995 |
| EP | 2 065 704 A1 | 6/2009 |
| GB | 874 742 A | 8/1961 |
| JP | 06 242095 A | 9/1994 |
| JP | 07 318545 A | 12/1995 |
| JP | 2009-183905 | 8/2009 |
| WO | WO 2005/111599 A1 | 11/2005 |
| WO | WO 2009/057256 A1 | 5/2009 |

OTHER PUBLICATIONS

U.S. Appl. No. 12/830,682—Final Office Action, mailed Apr. 29, 2013, 22 pages.
CN 2010-80031094.9—First Chinese Office Action, mailed Sep. 12, 2013, 15 pages.
CN 2009-80123127.X—Second Chinese Office Action, mailed Sep. 24, 2013, 13 pages.
EP 10 79 7800—EPO Supplementary European Search Report and European Search Opinion, dated Sep. 25, 2013, 6 pages.
U.S. Appl. No. 12/847,593—Final Office Action, mailed Jul. 18, 2013, 8 pages.
U.S. Appl. No. 12/847,593—Non-Final Office Action, mailed Dec. 20, 2012, 6 pages.
Tian, W. et al., "Microfabricated Preconcentrator-Focuser for a Microscale Gas Chromatograph," Journal of Microelectromechanical Systems, vol. 12, No. 3, Jun. 2003, pp. 264-272.
EP Application No. 09767436.0, Supplementary European Search Report and the European Search Opinion, Dec. 22, 2011, 8 pages.
PCT/US2011/033325, International Search Report and Written Opinion of the International Searching Authority, mail date Jan. 6, 2012, 7 pages.
Manolis, A., "The Diagnostic Potential of Breath Analysis," Clinical Chemistry, vol. 29, No. 1, pp. 5-15, (1983).
Ho, C. K. et al., "Review of Chemical Sensors for In-Situ Monitoring of Volatile Contaminants," Sandia Report, SAND2001-0643, pp. 1-28, (2001).
Riegel, J. et al., "Exhaust gas sensors for automotive emission control," Elsevier, Solid State Ionics 152-153, pp. 783-800, (2002).
Eranna, G. et al., "Oxide Materials for Development of Integrated Gas Sensors—A Comprehensive Review," Critical Reviews in Solid State and Materials Sciences, 29, pp. 111-188, (2004).
Arshak, K. et al., "A review of gas sensors employed in electronic nose applications," Sensor Review, vol. 24, No. 2, pp. 181-198, (2004).
Yamazoe, N., "Toward innovations of gas sensor technology," Elsevier, Sensors and Actuators B 108, pp. 2-14, (2005).
Cao, W. et al., "Breath Analysis: Potential for Clinical Diagnosis and Exposure Assessment," Clinical Chemistry 52, No. 5, pp. 800-811, (2006).
Buszewski, B. et al., "Human exhaled air analytics: biomarkers of diseases" Review, Biomedical Chromatography, 21, pp. 553-566, (2007).
Ohira, S.-I. et al., "Micro gas analyzers for environmental and medical applications," Elsevier, Science Direct, Analytica Chimica Acta 619, pp. 143-156, (2008).
Peng, G. et al., "Diagnosing lung cancer in exhaled breath using gold nanoparticles," Nature Nanotechnology, vol. 4, pp. 669-673, (2009).
Barnes, P. J. et al., "Exhaled Nitric Oxide in Pulmonary Diseases: A Comprehensive Review," Chest, Official publication of the American College of Chest Physicians, 138/3, pp. 682-692, (2010).
Rollins, G., "Beyond Breathalyzers: What Clinical Niche Will Breath Tests Fill?" Clinical Laboratory News, vol. 37, No. 5, pp. 1-6, (2011).
A. Hansel et al., "Proton transfer reaction mass spectrometry: on-line trace gas analysis at the ppb level," International Journal of Mass Spectrometry and Ion Processes, vols. 149-150, Nov. 15, 1995, pp. 609-619.
Y. Aimin et al., "Analysis of Gas by a Portable Gas Chromatograph With a Microwave Induced Plasma Ionization Detector," Chinese Journal of Analytical Chemistry, 1993, vol. 21, No. 6, pp. 736-739, w/ Abstract.

(56) References Cited

OTHER PUBLICATIONS

Auble, D.L. et al., "An open path, fast response infrared absorption gas analyzer for H2O and CO2," Boundary-Layer Meteorology, 1992, vol. 59, pp. 243-256.
Y. Haiying et al., "A New GC System for the Analysis of Permanent Gases," Rock and Mineral Analysis, Mar. 1999, vol. 18, No. 1, pp. 29-33, Beijing, China.
B. Shi, "Application of 4 200 Ultra-fast GC Analyzer to Environment Emergence Monitoring," Liaoning Urban and Rural Environmental Science & Technology, 2006, vol. 26, No. 6, pp. 34-35.
JP 2011-514674—First Japanese Office Action, mailed Nov. 12, 2013, 5 pages.
CN 2010-80040138.4—First Chinese Office Action, mailed Oct. 28, 2013, 25 pages.
U.S. Appl. No. 12/847,593—Notice of Allowance, mailed Nov. 19, 2013, 11 pages.
U.S. Appl. No. 13/332,064—Notice of Allowance, mailed Nov. 25, 2013, 12 pages.
Abstract of Liu Juntao et al., "Multi-Dimensional Gas Chromatography for Analysis of Refinery Gas," Modern Instruments, vol. 6, pp. 48-51, (2004).
CN 2011-80026437.7—First Chinese Office Action, issued Jan. 6, 2014, 41 pages.
Wohltjen, H. et al., "Colloidal Metal-Insulator-Metal Ensemble Chemiresistor Sensor," Analytical Chemistry, vol. 70, No. 14, Jul. 15, 1998, pp. 2856-2859.
Dutta, R. et. al., "Bacteria Classification using Cyranose 320 Electronic Nose," BioMedical Engineering OnLine 2002, Published: Oct. 16, 2002, 7 pages.
Lambertus, G. et. al., "Design, Fabrication, and Evaluation of Microfabricated Columns for Gas Chromatography," Analytical Chemistry, vol. 76, No. 9, May 1, 2004, pp. 2629-2637.
Hanson III, C.W. et al., "Electronic Nose Prediction of a Clinical Pneumonia Score: Biosensors and Microbes," Anesthesiology, V 102, No. 1, Jan. 2005, pp. 63-68.
Tian, W. et al., "Multiple-Stage Microfabricated Preconcentrator-Focuser for Micro Gas Chromatography System," Journal of Microelectromechanical Systems, vol. 14, No. 3, Jun. 2005, pp. 498-507.
Phillips, M. et. al., "Volatile Biomarkers of Pulmonary Tuberculosis in the Breath," Tuberculosis, (2007) 87, pp. 44-52.
Phillips, M. et. al., "Prediction of Lung Cancer using Volatile Biomarkers in Breath," Cancer Biomarkers, 3, (2007), pp. 95-109.
Rowe, M.P. et. al., "Exploiting Charge-Transfer Complexation for Selective Measurement of Gas-Phase Olefins with Nanoparticle-Coated Chemiresistors," Analytical Chemistry, vol. 79, No. 3, Feb. 1, 2007, pp. 1164-1172.
Bae, B. et al., "A Fully-Integrated MEMS Preconcentrator for Rapid Gas Sampling," Transducers & Eurosensors'07, The 14$^{th}$ International Conference on Solid-State Sensors, Actuators and Microsystems, Lyon, France, Jun. 10-14, 2007, 2007 IEEE, pp. 1497-1500.
U.S. Notice of Allowance mailed Aug. 30, 2011, U.S. Appl. No. 12/140,822, filed Jun. 17, 2008, 9 pages.
Libardoni, M. et al., "Analysis of human breath samples with a multi-bed sorption trap and comprehensive two-dimensional gas chromatography (GC×GC)," Elsevier, Science Direct, Journal of Chromatography B, 842, (2006), pp. 13-21.
de Alencastro, L. F. et al., "Application of Multidimensional (Heart-Cut) Gas Chromatography to the Analysis of Complex Mixtures of Organic Pollutants in Environmental Samples," Environmental Analysis, Chimia 57, No. 9, (2003) pp. 499-504.
Lambertus, G. et al., "Stop-Flow Programmable Selectivity with a Dual-Column Ensemble of Microfabricated Etched Silicon Columns and Air as Carrier Gas," Analytical Chemistry, vol. 77, No. 7, Apr. 1, 2005, pp. 2078-2084.
Phillips, M. et al., "Breath biomarkers of active pulmonary tuberculosis," Elsevier, Diagnostics, Tuberculosis (2010) pp. 1-7.
PCT/US2009/045872, International Search Report and Written Opinion of the International Searching Authority, mail date Jul. 27, 2009, 11 pages.
PCT/US2010/041243, International Search Report and Written Opinion of the International Searching Authority, mail date Feb. 17, 2011, 7 pages.
PCT/US2010/044165, International Search Report and Written Opinion of the International Searching Authority, mail date Apr. 29, 2011, 8 pages.
U.S. Office Action mailed Dec. 22, 2010, U.S. Appl. No. 12/140,822, filed Jun. 17, 2008, 16 pages.
U.S. Office Action mailed May 18, 2011, U.S. Appl. No. 12/140,822, filed Jun. 17, 2008, 6 pages.
U.S. Appl. No. 12/830,682—Non-Final Office Action, mailed Sep. 4, 2012, 21 pages.
U.S. Appl. No. 13/332,064—Non-Final Office Action, mailed Nov. 5, 2012, 24 pages.
CN 200980123127.X—First Chinese Office Action, issued Feb. 1, 2013, 27 pages.
CN 2009-80123127.X—Second Chinese Office Action, issued Apr. 21, 2014, 12 pages.
CN 2011-514674—Notice of Allowance, issued Jun. 19, 2014, 3 pages.
CN 2010-80040138.4—Notice of Allowance, mailed Feb. 20, 2014, 13 pages.

* cited by examiner

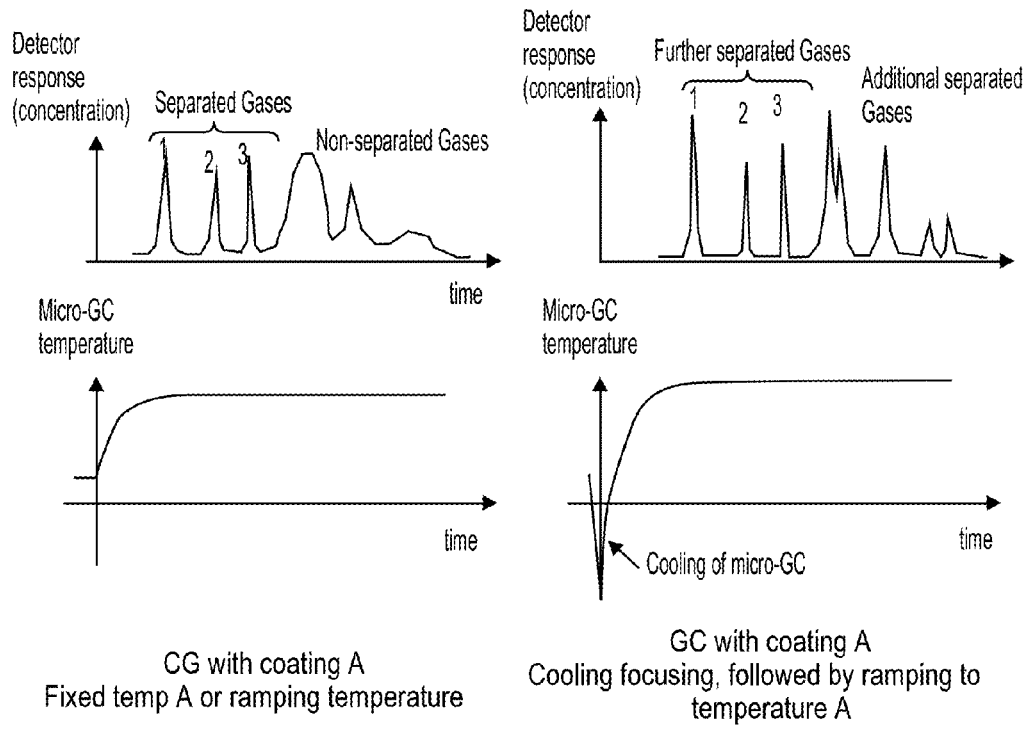
Fig. 11A
Fig. 11B
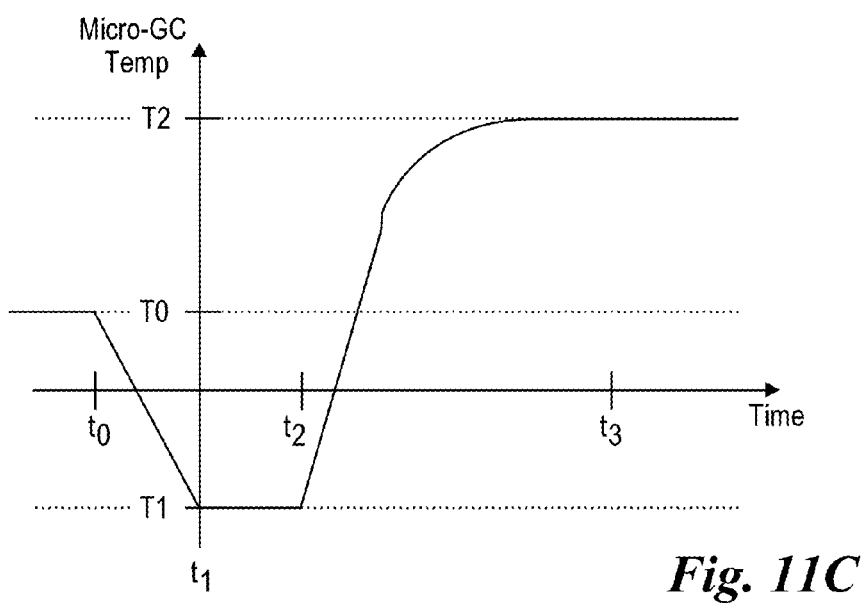
Fig. 11C

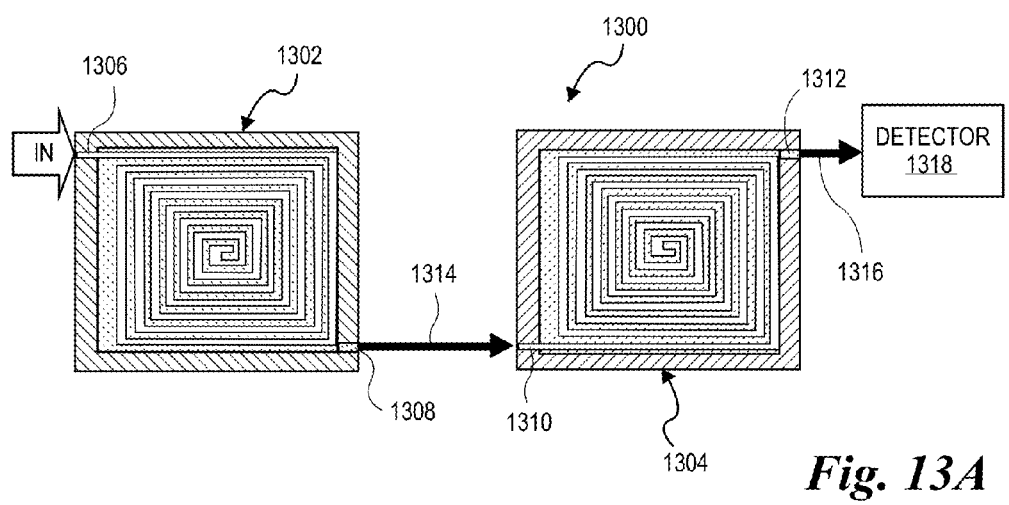
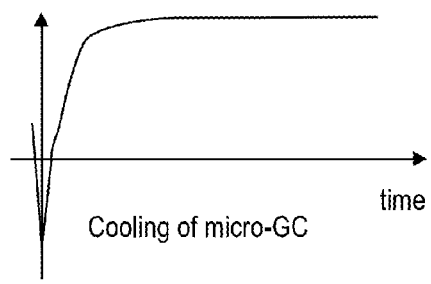
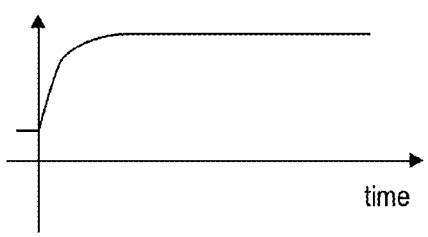
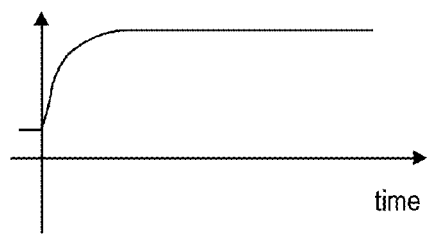
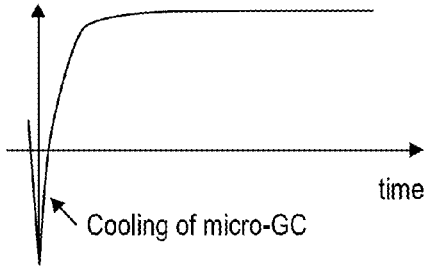
*Fig. 13B*    *Fig. 13C*

GAS ANALYTE SPECTRUM SHARPENING AND SEPARATION WITH MULTI-DIMENSIONAL MICRO-GC FOR GAS CHROMATOGRAPHY ANALYSIS

CROSS-REFERENCE TO RELATED APPLICATIONS

This application claims priority under 35 U.S.C. §119(e) to U.S. Provisional Patent Application No. 61/327,392, filed 23 Apr. 2010, and whose entire contents are hereby incorporated by reference.

TECHNICAL FIELD

The present disclosure relates generally to gas chromatography and in particular, but not exclusively, to gas chromatography with gas analyte spectrum sharpening and separation using individual, cascaded and/or multi-dimensional micro gas chromatographs (micro-GCs).

BACKGROUND

Gas analysis can be an important means for detecting the presence and concentration of certain chemicals in the gas and determining the meaning of the particular combination of chemicals present. In health care, for example, the presence of certain volatile organic compounds (VOCs) in exhaled human breath are correlated to certain diseases, such as pneumonia, pulmonary tuberculosis (TB), asthma, lung cancer, liver diseases, kidney diseases, etc. The correlations are especially evidential for lung-related diseases. In other applications, gas analysis can be used to determine the presence of dangerous substances incompatible with human presence, such as methane, carbon monoxide or carbon dioxide in a mine.

Current gas analytical systems still rely heavily on large and expensive laboratory instruments, such as gas chromatography (GC) and mass spectrometry (MS). Most of these instruments (mass spectrometers in particular) have operational characteristics that prevent significant reductions in their size, meaning that current gas analysis systems are large and expensive bench devices. In addition to being expensive and unwieldy, the large size of current gas analysis devices makes widespread use of these instruments impossible.

GC column coatings are usually optimized for specific temperatures and chemicals, so that no single GC can separate a large array of chemicals, even by varying its temperature. Because existing GCs are large, heavy units housed in labs, a carrier gas with many chemicals may need to be sent to multiple locations for separation, which substantially increases cost. The gas analyte/volatile organic compound (VOC) concentration distribution (spectrum) usually is broadened when injected into the GC column. In the application of portable gas analysis, there is no viable solution to sharpen the analyte/VOC spectrum without loss of detection limit. Moreover, the current column focusing can only be achieved by direct impinging liquid nitrogen or dry ice to a small section of bulky GC column for focusing effect. Such approach is expensive and cannot be implemented as a portable gas analysis system.

BRIEF DESCRIPTION OF THE DRAWINGS

Non-limiting and non-exhaustive embodiments of the present invention are described with reference to the following Figs., wherein like reference numerals refer to like parts throughout the various views unless otherwise specified.

FIG. 11A is a graph of an embodiment of a detector response to an embodiment of a temperature profile applied to a gas chromatograph.

FIG. 11B is a graph of an embodiment of a detector response to an alternative embodiment of a temperature profile applied to a gas chromatograph.

FIG. 11C is a graph of an embodiment of a temperature profile for a gas chromatograph.

FIG. 13A is a schematic of an embodiment of a cascaded gas chromatograph.

FIGS. 13B-13C are graphs of embodiments of temperature profiles that can be applied to the cascaded gas chromatograph of FIG. 13A.

DETAILED DESCRIPTION OF THE ILLUSTRATED EMBODIMENTS

Embodiments of an apparatus, process and system for gas analysis in point-of-care medical applications are described herein. In the following description, numerous specific details are described to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail but are nonetheless encompassed within the scope of the invention.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in this specification do not necessarily all refer to the same embodiment. Furthermore, the particular features, structures, or characteristics may be combined in any suitable manner in one or more embodiments.

Figure 1A:
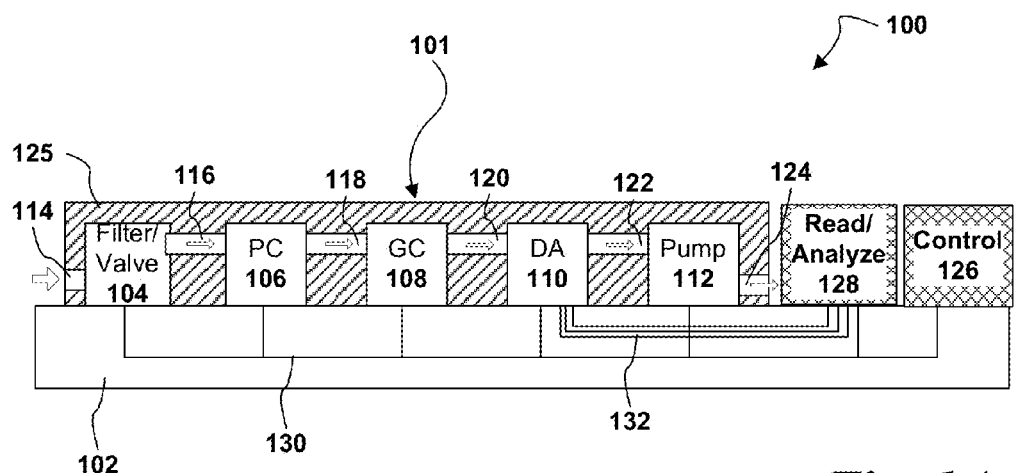
FIG. 1A is a side elevation drawing of an embodiment of a gas analysis device.
Figure 1B:
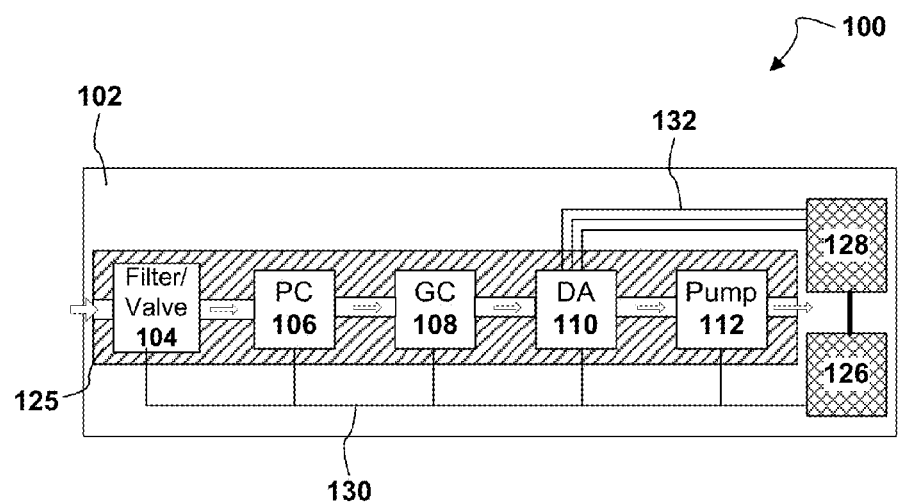
FIG. 1B is a plan view of the embodiment of a gas analysis device shown in FIG. 1.

FIGS. 1A and 1B together illustrate an embodiment of a small scale (e.g., handheld) gas analysis device 100. Device 100 includes a substrate 102 on which are mounted a fluid handling assembly 101, a controller 126 coupled to the individual elements within fluid handling assembly 101, and a reading and analysis circuit 128 coupled to detector array 110 and to controller 126. The embodiment shown in the Figs. illustrates one possible arrangement of the elements on substrate 102, but in other embodiments the elements can, of course, be arranged on the substrate differently.

Substrate 102 can be any kind of substrate that provides the required physical support and communication connections for the elements of device 100. In one embodiment, substrate 102 can be a printed circuit board (PCB) of the single-layer variety with conductive traces on its surface, but in other embodiments it can be a PCB of the multi-layer variety with conductive traces in the interior of the circuit board. In other embodiments, for example an embodiment where device 100 is built as a monolithic system on a single die, substrate 102 can be chip or wafer made of silicon or some other semiconductor. In still other embodiments, substrate 102 can also be a chip or wafer in which optical waveguides can be formed to support optical communication between the components of device 100.

Fluid handling assembly 101 includes a filter and valve assembly 104, a pre-concentrator 106, a gas chromatograph 108, a detector array 110 and a pump 112. Elements 104-112 are fluidly coupled in series: filter and valve assembly 104 is fluidly coupled to pre-concentrator 106 by fluid connection 116, pre-concentrator 106 is fluidly coupled to gas chromatograph 108 by fluid connection 118, gas chromatograph 108 is fluidly coupled to detector array 110 by fluid connection 120, and detector array 110 is coupled to pump 112 by fluid connection 122. As further described below, in one embodiment of device 100 elements 104-112 can be micro-electro-mechanical (MEMS) elements or MEMS-based elements, meaning that some parts of each device can be MEMS and other parts not. In other embodiments of device 100, some or all of elements 104-112 need not be MEMS or MEMS-based, but can instead be some non-MEMS chip scale device.

As indicated by the arrows in the Figs., the fluid connections between elements 104-112 allow a fluid (e.g., one or more gases) to enter filter and valve assembly 104 through inlet 114, flow though elements 104-112, and finally exit pump 112 through outlet 124. Fluid handling assembly 101 also includes a shroud or cover 125 that protects individual elements 104-112. In the illustrated embodiment, channels formed in shroud 125 provide the fluid connections between the elements, but in other embodiments the fluid connections between elements can be provided by other means, such as tubing. In still other embodiments shroud 125 can be omitted.

Filter and valve assembly 104 includes an inlet 114 and an outlet coupled to fluid connection 116 such that fluid exiting filter and valve assembly 104 flows into pre-concentrator 106. Filter and valve assembly 104 includes a filter to remove particulates from fluid entering through inlet 114. In embodiments of device 100 where one or more of elements 104-112 is a MEMS element, the small scale of parts within the MEMS elements means that fluid entering through inlet 114 might need to be filtered to remove these particles so that the particles do not enter the MEMS elements and either them or render them inoperative. In embodiments of device 100 that include no MEMS components, or where fluid entering inlet 114 contains no particles, for instance because it has been pre-filtered externally to device 100, the filter portion of filter and valve assembly 104 can be omitted.

Filter and valve assembly 104 also includes a valve so that further flow through inlet 114 into fluid handling assembly 101 can be stopped once sufficient fluid has passed through the device. Stopping further flow through inlet 114 prevents dilution of fluids that will flow out of pre-concentrator 106 during later operation of device 100 (see description of operation below). In other embodiments, filter and valve assembly 104 can also include a de-humidifier to remove water vapor from the fluid entering through inlet 114, thus improving the accuracy and sensitivity of device 100.

Pre-concentrator 106 includes an inlet coupled to fluid connection 116 and an outlet coupled to fluid connection 118. Pre-concentrator 106 receives fluid from filter and valve assembly 104 through fluid connection 116 and outputs fluid to gas chromatograph 108 through fluid connection 118. As fluid flows through pre-concentrator 106, the pre-concentrator absorbs certain chemicals from the passing fluid, thus concentrating those chemicals for later separation and detection. In one embodiment of device 100 pre-concentrator 106 can be a MEMS pre-concentrator, but in other embodiments pre-concentrator 106 can be a non-MEMS chip scale device. Further details of an embodiment of a MEMS pre-concentrator are described below in connection with FIG. 2.

Figure 14A:
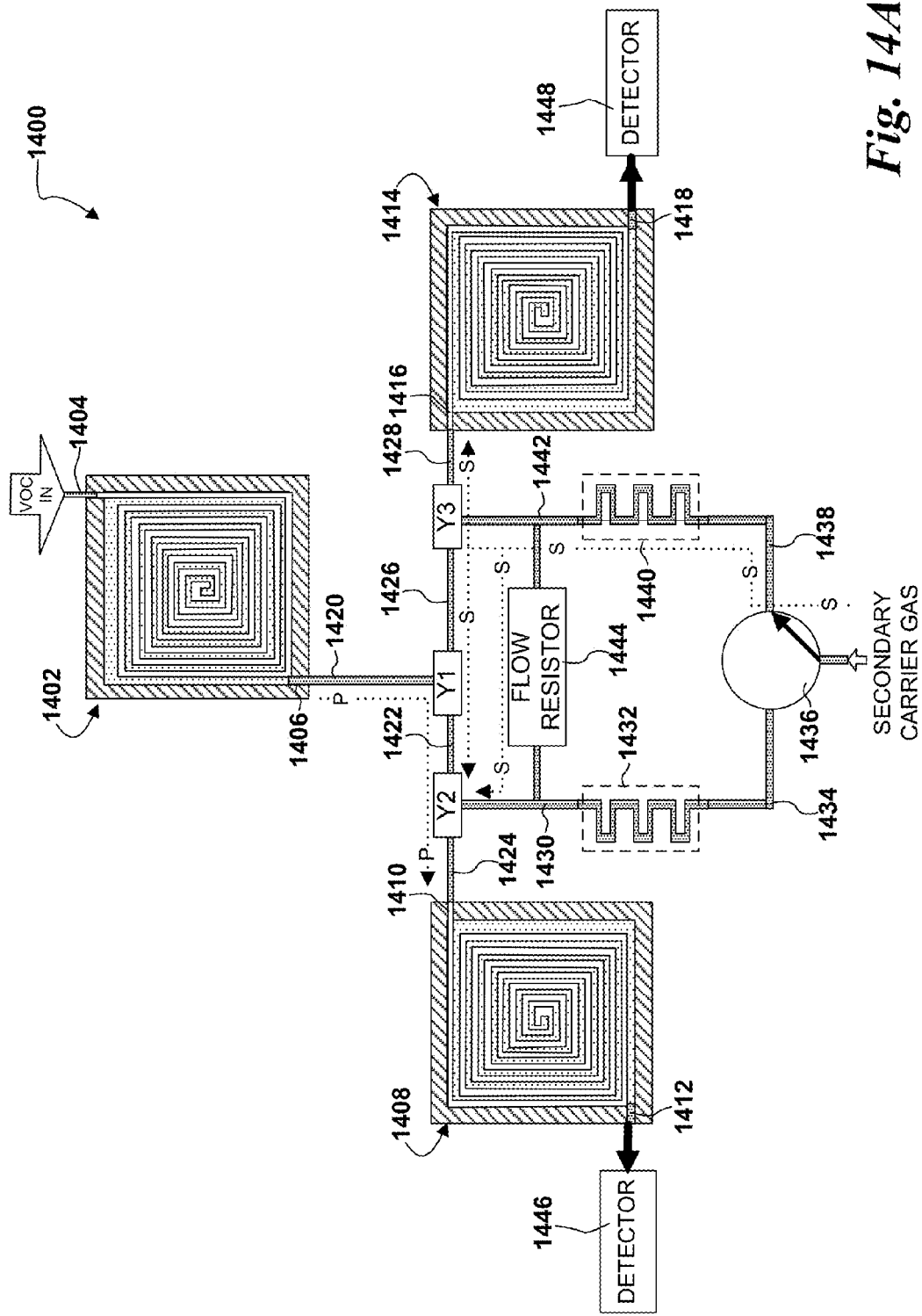
FIGS. 14A-14B are schematics of an embodiment of a multi-dimensional gas chromatograph.

Gas chromatograph 108 includes an inlet coupled to fluid connection 118 and an outlet coupled to fluid connection 120. Gas chromatograph 108 receives fluid from pre-concentrator 106 through fluid connection 118 and outputs fluid to detector array 110 through fluid connection 120. As fluid received from pre-concentrator 106 flows through gas chromatograph 108, individual chemicals in the fluid received from the pre-concentrator are separated from each other in the time domain for later input into detector array 110. In one embodiment of device 100 gas chromatograph 108 can be a MEMS gas chromatograph, but in other embodiments gas chromatograph 108 can be a non-MEMS chip scale device. Further details of an embodiment of a MEMS gas chromatograph 108 are described below in connection with FIGS. 3A-3C. Although shown in the drawing as a single chromatograph, in other embodiments gas chromatograph 108 can be any of the gas chromatographs shown in FIG. 10 et seq. In an embodiment in which gas chromatograph 108 includes multiple chromatographs, it can be necessary to adjust the number of downstream and/or upstream components in device 100 to coincide with the input or output configuration of the gas chromatograph. For instance, if the chromatograph 1400 shown in FIG. 14A is used as chromatograph 108 in device 100, it can be necessary to adjust the number of detector arrays 110, pumps 112, and so forth, to correspond to the number of outputs of chromatograph 1400.

Detector array 110 includes an inlet coupled to fluid connection 120 and an outlet coupled fluid connection 122. Detector array 110 receives fluid from gas chromatograph 108 through fluid connection 120 and outputs fluid to pump 112 through fluid connection 122. As fluid flows through detector array 110, the chemicals that were time-domain separated by gas chromatograph 108 enter the detector array and their presence and/or concentration is sensed by sensors within the detector array. In one embodiment of device 100 detector array 110 can be a MEMS detector array, but in other embodiments detector array 110 can be a non-MEMS chip scale device. Further details of an embodiment of a detector array 110 are described below in connection with FIG. 4. Although shown in the Fig. as a single detector array, in other embodiments detector array 110 can actually include multiple detector arrays. For example, in an embodiment where gas chromatograph 108 is a configuration made up of several individual chromatographs, such as chromatograph 1400 shown in FIG. 14, it can be necessary to adjust the number of detector arrays to match the output configuration of the cascaded chromatographs.

Pump 112 includes an inlet coupled to fluid connection 122, as well as an outlet coupled to an exhaust 124, such that pump 112 draws fluid from detector array 110 through fluid connections 122 and returns it to the atmosphere through exhaust 124. Pump 112 can be any kind of pump that meets the size and form factor requirements of device 100, provides the desired flow rate and flow rate control, and has adequate reliability (i.e., adequate mean time between failures (MTBF)). In one embodiment, pump 112 can be a MEMS or MEMS-based pump, but in other embodiments it can be another type of pump. Examples of pumps that can be used include small axial pumps (e.g., fans), piston pumps, and electro-osmotic pumps. Although shown in the Fig. as a single pump, in other embodiments pump 112 can actually be made up of multiple pumps. For example, in an embodiment where gas chromatograph 108 is a cascaded configuration made up of several individual chromatographs, such as chromatograph 1400 shown in FIG. 14, it can be necessary to adjust the number of pumps to match the output configuration of the cascaded chromatographs.

Controller 126 is communicatively coupled to the individual elements within fluid handling assembly 101 such that it can send control signals and/or receive feedback signals from the individual elements. In one embodiment, controller 126 can be an application-specific integrated circuit (ASIC) designed specifically for the task, for example a CMOS controller including processing, volatile and/or non-volatile storage, memory and communication circuits, as well as associated logic to control the various circuits and communicate externally to the elements of fluid handling assembly 101. In other embodiments, however, controller 126 can instead be a general-purpose microprocessor in which the control functions are implemented in software. In the illustrated embodiment controller 126 is electrically coupled to the individual elements within fluid handling assembly 101 by conductive traces 130 on the surface or in the interior of substrate 102, but in other embodiments controller 126 can be coupled to the elements by other means, such as optical.

Readout and analysis circuit 128 is coupled to an output of detector array 110 such that it can receive data signals from individual sensors within detector array 110 and process and analyze these data signals. In one embodiment, readout and analysis circuit 128 can be an application-specific integrated circuit (ASIC) designed specifically for the task, such as a CMOS controller including processing, volatile and/or non-volatile storage, memory and communication circuits, as well as associated logic to control the various circuits and communicate externally. In other embodiments, however, readout and analysis circuit 128 can instead be a general-purpose microprocessor in which the control functions are implemented in software. In some embodiments readout and analysis circuit 128 can also include signal conditioning and processing elements such as amplifiers, filters, analog-to-digital converters, etc., for both pre-processing of data signals received from detector array 110 and post-processing of data generated or extracted from the received data by readout and analysis circuit 128.

In the illustrated embodiment, readout and analysis circuit 128 is electrically coupled to detector array 110 by conductive traces 132 positioned on the surface or in the interior of substrate 102, but in other embodiments controller 126 can be coupled to the elements by other means, such as optical means. Readout and analysis circuit 128 is also coupled to controller 126 and can send signals to, and receive signals from, controller 126 so that the two elements can coordinate and optimize operation of device 100. Although the illustrated embodiment shows controller 126 and readout and analysis circuit 128 as physically separate units, in other embodiments the controller and the readout and analysis circuit could be combined in a single unit.

In operation of device 100, the system is first powered up and any necessary logic (i.e., software instructions) is loaded into controller 126 and readout and analysis circuit 128 and initialized. After initialization, the valve in filter and valve unit 104 is opened and pump 112 is set to allow flow through the fluid handling assembly. Fluid is then input to fluid handling assembly 101 through inlet 114 at a certain flow rate and/or for a certain amount of time; the amount of time needed will usually be determined by the time needed for pre-concentrator 106 to generate adequate concentrations of the particular analytes (e.g., chemicals or VOCs) whose presence and/or concentration are being determined. As fluid is input to the system through inlet 114, it is filtered by filter and valve assembly 104 and flows through elements 104-112 within fluid handling assembly 101 by virtue of the fluid connections between these elements. After flowing through elements 104-112, the fluid exits the fluid handling assembly through exhaust 124.

After the needed amount of fluid has been input through inlet 114, the valve in filter and valve assembly 104 is closed to prevent further input of fluid. After the valve is closed, a heater in pre-concentrator 106 activates to heat the pre-concentrator. The heat releases the chemicals absorbed and concentrated by the pre-concentrator. As the chemicals are released from pre-concentrator 106, pump 112 is activated to draw the released chemicals through gas chromatograph 108 and detector array 110 and output the chemicals through exhaust 124. Activation of pump 112 also prevents backflow through fluid handling assembly 101.

As the chemicals released from pre-concentrator 106 are drawn by pump 112 through gas chromatograph 108, the chromatograph separates different chemicals from each other in the time domain—that is, different chemicals are output from the gas chromatograph at different times. As the different chemicals exit gas chromatograph 108 separated in time, each chemical enters MEMS detection array 110, where sensors in the detection array detect the presence and/or concentration of each chemical. The time-domain separation performed in gas chromatograph 108 substantially enhances the accuracy and sensitivity of MEMS detection array 110, since it prevents numerous chemicals from entering the detection array at the same time and thus prevents cross-contamination and potential interference in the sensors within the array.

As individual sensors within MEMS detection array 110 interact with the entering time-domain-separated chemicals, the detection array senses the interaction and outputs a signal to readout and analysis circuit 128, which can then use the signal to determine presence and/or concentration of the chemicals. When readout and analysis circuit 128 has determined the presence and/or concentration of all the chemicals of interest it can use various analysis techniques, such as correlation and pattern matching, to extract some meaning from the particular combination of chemicals present and their concentrations.

Figure 2A:
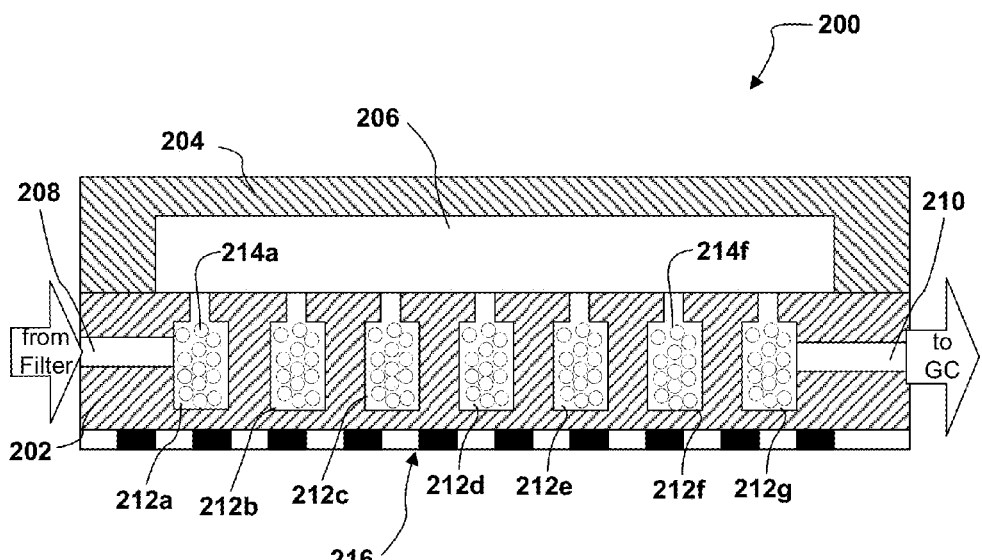
FIG. 2A is a cross-sectional elevation drawing of an embodiment of a MEMS pre-concentrator that can be used in the embodiment of a gas analysis device shown in FIGS. 1A-1B.

FIG. 2A illustrates an embodiment of a MEMS pre-concentrator 200 that can be used as pre-concentrator 106 in device 100. Pre-concentrator 200 includes a substrate 202 having a cover plate 204 bonded thereto and sealed around the perimeter of the substrate to create a cavity 206. Substrate 202 has formed therein an inlet 208 on one side, an outlet 210 on a different side, and pockets 212a-212g having absorbents therein. In one embodiment, substrate 202 is a silicon substrate, but in other embodiments substrate 202 can of course be made of other materials. Heater 216 is formed on the side of substrate 202 opposite the side where cover plate 204 is attached.

In an embodiment where substrate 202 is silicon, inlet 208, outlet 210 and pockets 212a-212g can be formed using standard photolithographic patterning and etching. Although the illustrated embodiment shows seven pockets 212a-212g, the number of pockets needed depends on the number of different chemicals to be absorbed and concentrated, and on the nature of the absorbents used. In an embodiment where each absorbent absorbs only one chemical, the number of pockets 212a-212g can correspond exactly to the number of chemicals to be absorbed and concentrated, but in other embodiments where each absorbent absorbs only one chemical a greater number of pockets can be used to increase the absorption area. In still other embodiments where each absorbent can absorb more than one chemical, a lesser number of pockets can be used.

Each pocket 212 has a corresponding absorbent 214 in its interior-pocket 212a has absorbent 214a, pocket 212b has absorbent 214b, and so on. Although shown in the illustrated embodiment as a granular absorbent, in other embodiments absorbents 214 can be coatings on the walls of pockets 212 or can be a continuous substance that partially or fully fills each pocket 212. Other embodiments can include combinations of granular, wall coatings or continuous filling absorbents. Each absorbent can have a chemical affinity for one or more particular chemicals, meaning that the exact absorbents used will depend on the number and nature of chemicals to be absorbed and concentrated. Examples of absorbents that can be used include Carbopack B, Carbopack X, etc.

During operation of MEMS pre-concentrator 200 in device 100, fluid from filter and valve assembly 104 enters through inlet 208, passes through absorbent 214a in pocket 212a, and enters cavity 206. Cover plate 204 helps guide fluid entering the cavity 206 into the different pockets 212b-212g and through absorbents 214b-214g, until the fluid, minus the chemicals absorbed by absorbents 214a-214g, exits the pre-concentrator through outlet 210. Once enough fluid has flowed through the pre-concentrator, the valve in filter and valve assembly 104 is closed to prevent further flow through inlet 208. Heater 216 is then activated. Heater 216 heats absorbents 214a-214f, causing them to release the absorbed chemicals through processes such as outgassing. Simultaneously with activating heater 216, or shortly thereafter, pump 112 is activated, drawing the released chemicals out through outlet 210 to gas chromatograph 108.

Figure 2B:
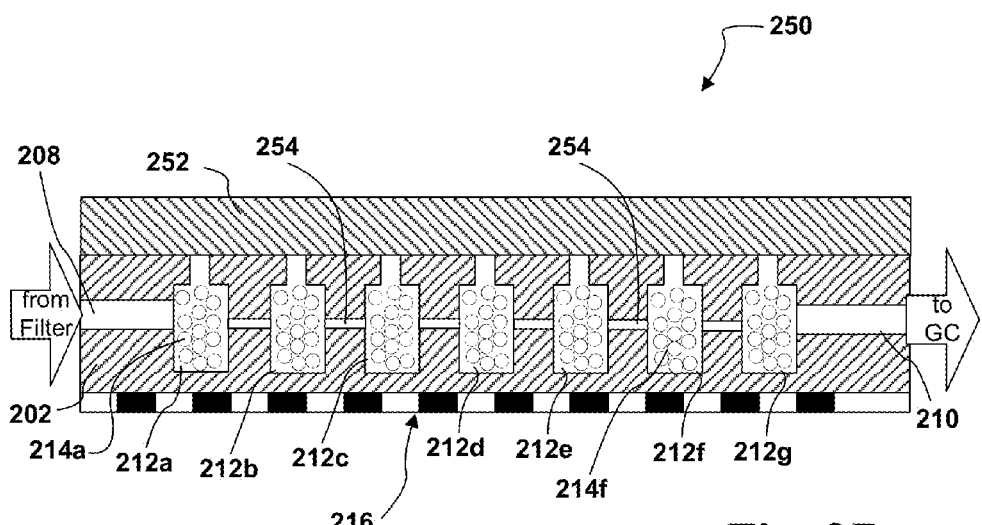
FIG. 2B is a cross-sectional elevation drawing of an alternative embodiment of a MEMS pre-concentrator that can be used in the embodiment of a gas analysis device shown in FIGS. 1A-1B.

FIG. 2B illustrates an alternative embodiment of a MEMS pre-concentrator 250. MEMS pre-concentrator 250 is in many respects similar to MEMS pre-concentrator 200. The primary difference between the two is that in MEMS pre-concentrator 250, the cover plate 252 is directly bonded to the substrate 202 without formation of cavity 206 found in cover plate 252. In one embodiment of MEMS pre-concentrator 250, channels/openings 254 can exist in substrate 202 between the different pockets 212a-212g to allow the fluid to flow through adjacent pockets. In operation of MEMS pre-concentrator 250, fluid enters through inlet 208, passes through the different pockets 212a-212g via the channels/openings 254 between the pockets, and finally exits the pre-concentrator through outlet 210.

Figure 3A:
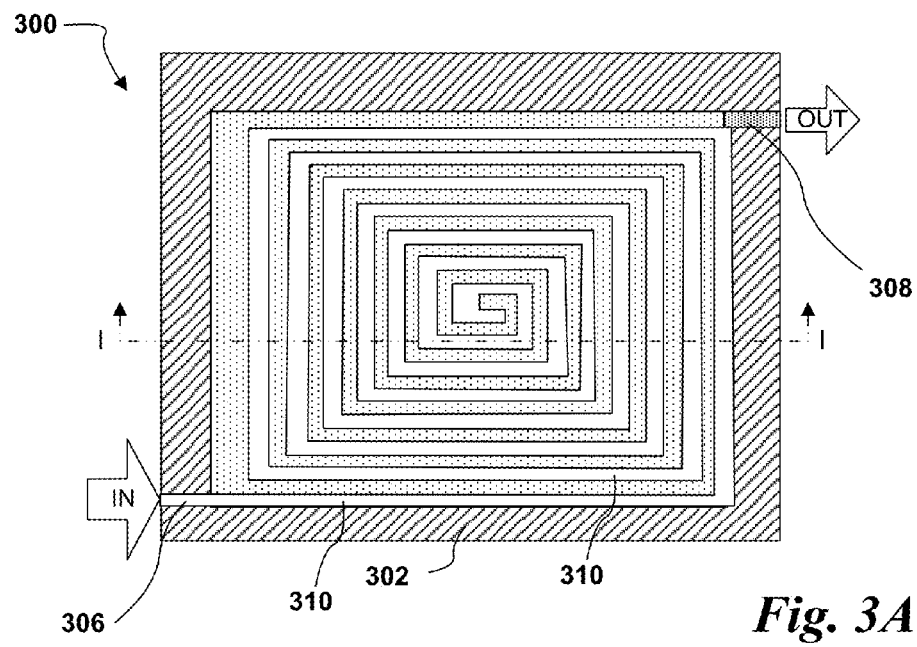
FIG. 3A is a plan view drawing of an embodiment of a MEMS gas chromatograph that can be used in the embodiment of a gas analysis device shown in FIGS. 1A-1B.
Figure 3B:
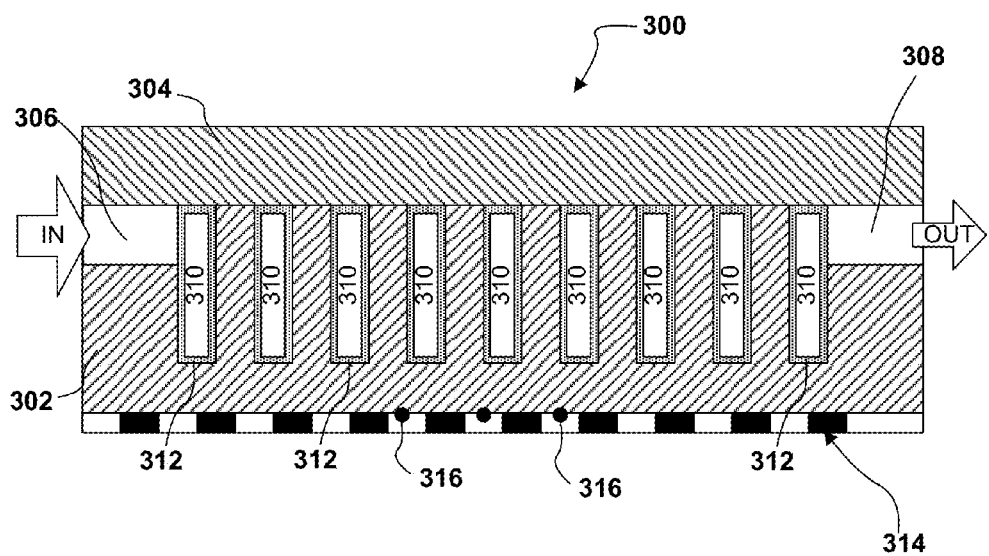
FIG. 3B is a cross-sectional elevation drawing of the embodiment of a MEMS gas chromatograph shown in FIG. 3A, taken substantially along section line I-I.

FIGS. 3A-3B illustrate embodiments of an individual MEMS gas chromatograph 300 that can be used as GC 108 in device 100. MEMS gas chromatograph 300 includes a substrate 302 with an inlet 306 on one side, an outlet 308 on a different side, and a separation column 310 having a stationary phase coating on its walls. A cover plate 304 is bonded to substrate 302 to seal column 310. In one embodiment substrate 302 is a silicon substrate, but in other embodiments substrate 302 can of course be made of other materials. In an embodiment where substrate 302 is silicon, inlet 306, outlet 308 and column 310 can be formed using standard photolithographic patterning and etching, such as deep reactive ion etching (DRIE). Temperature control 314 is formed on the side of substrate 302 opposite the side where cover plate 204 is attached. In one embodiment, temperature control is integrated with chromatograph 300 and can include heating elements and/or cooling elements, or elements that are capable of both heating and cooling such as a Peltier device or thermoelectric cooler (TEC). In embodiments where GC 300 is small (~1 inch range in one embodiment), it can be heated and cooled quickly with these devices. Temperature control 314 can also include one or more temperature sensors 316 to allow for monitoring and/or feedback control of temperature control 314.

Channel or column 310 provides a continuous fluid path from inlet 306 to outlet 308, and some or all of the walls of column 310 are coated with a stationary phase coating that can interact with the chemicals being separated by the chromatograph or, in other words, the column walls are coated with specific materials that have specific selectivity/separation power for the desired gas analysis. How thoroughly and how fast chemicals are separated from the fluid depend on the stationary phase coating, the overall path length of column 310, and the temperature. For a given stationary phase coating, the longer the column the better the chemical spectrum separation, but a long column also extends the separation time. For a given application, the required path length will therefore usually be determined by a tradeoff among the coating, the column length and the temperature. The illustrated embodiment shows column 310 as a spiral column in which the column path length will depend on the number of coils in the spiral. In other embodiments, however, column 310 can be shaped differently. In one embodiment, column 310 can be between 1 m and 10 m in length, but in other embodiment can be outside this range. In the illustrated MEMS GC, column 310 can be formed by micromachining or micro-electro-mechanical-systems (MEMS) process on silicon wafer, glass wafer, PCB board, or any type of substrate.

During operation of MEMS gas chromatograph 300 in device 100, fluid from pre-concentrator 106 enters through inlet 306 and passes through column 310. As fluid passes through the column 310, the different chemicals in the fluid interact with stationary phase coating 312 at different rates, meaning that the chemicals are separated after traveling through the column, with the chemicals that interact strongly with the stationary phase being separated first and the chemicals that interact weakly with the stationary phase being separated last. In other words, chemicals that interact strongly with the stationary phase are retained longer in the stationary phase, while chemicals that interacted weakly with the stationary phase retained less time in the stationary phase. In some embodiments of gas chromatograph 300 this time-domain separation can occur according to molecular weight (e.g., chemicals with the lowest molecular weight are separated first, followed by higher molecular weights), but in other embodiments it can occur according to other chemical characteristics or other separation mechanisms. As the chemicals are time-domain separated, pump 112 draws them out of MEMS gas chromatograph 300 through outlet 308. Generally, the chemicals exit through outlet 308 in the reverse order of their separation—that is, chemicals with low retention time exit first, while chemicals with higher retention times exit later. After leaving outlet 308, the chemicals enter detector array 110.

Figure 3C:
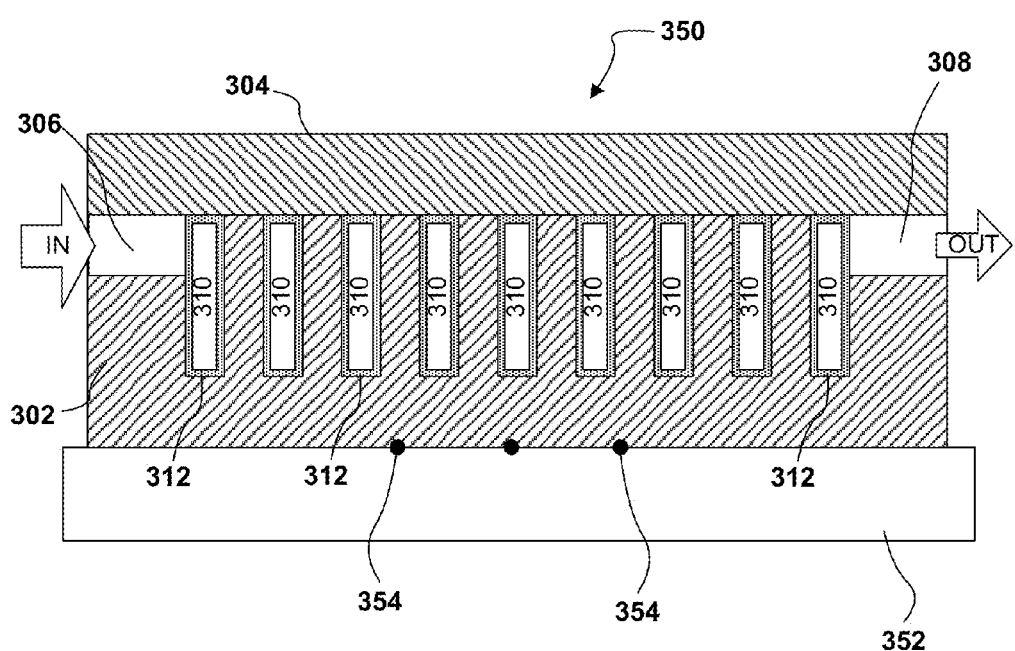
FIG. 3C is a cross-sectional elevation drawing of an alternative embodiment of the MEMS gas chromatograph shown in FIG. 3B.

FIG. 3C illustrates an alternative embodiment of an individual gas chromatograph 350. Gas chromatograph 350 is in most respects similar to gas chromatograph 300 shown in FIG. 3B. The primary difference between gas chromatographs 300 and 350 is the configuration of the temperature control. In gas chromatograph 350, temperature control 352 is not integrated into the chromatograph, but instead is an external component, such as a Peltier device, a thermo-electric cooler (TEC) or a heating and/or cooling plate, that is thermally coupled to the chromatograph. Thermal coupling between external temperature control 352 and the chromatograph can be accomplished, for example, using thermally conductive adhesives or with thermal interface materials. As with temperature control 314, temperature control 352 can include one or more temperature sensors 354 to monitor the temperature and/or provide feedback control of the temperature control. Since the GC is small (about 1 inch range in one embodiment, but not limited to this range), fast heating and cooling control can be achieved with either the integrated or external temperature controls.

Figure 3D:
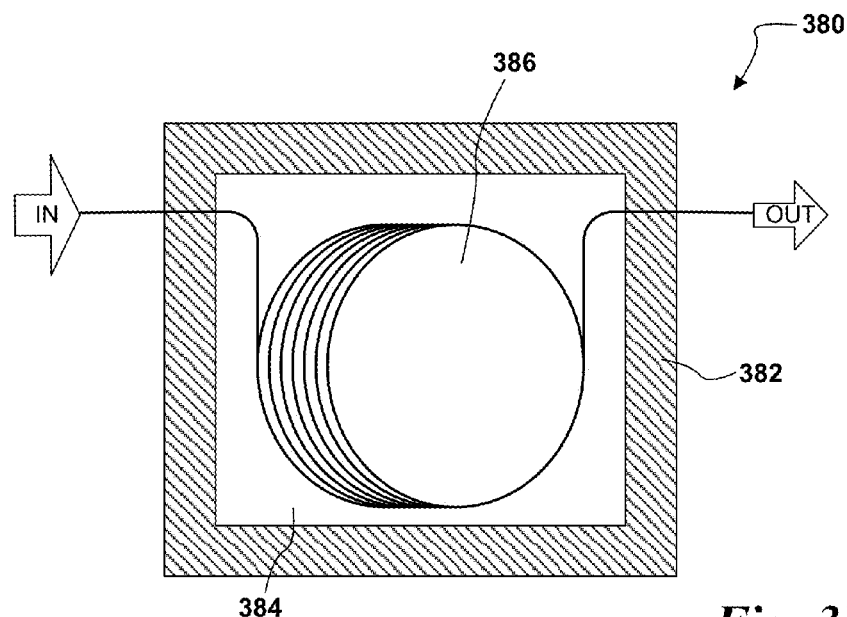
FIG. 3D is a plan view of an alternative embodiment of a gas chromatograph that can be used in the embodiment of a gas analysis device shown in FIGS. 1A-1B.
Figure 3E:
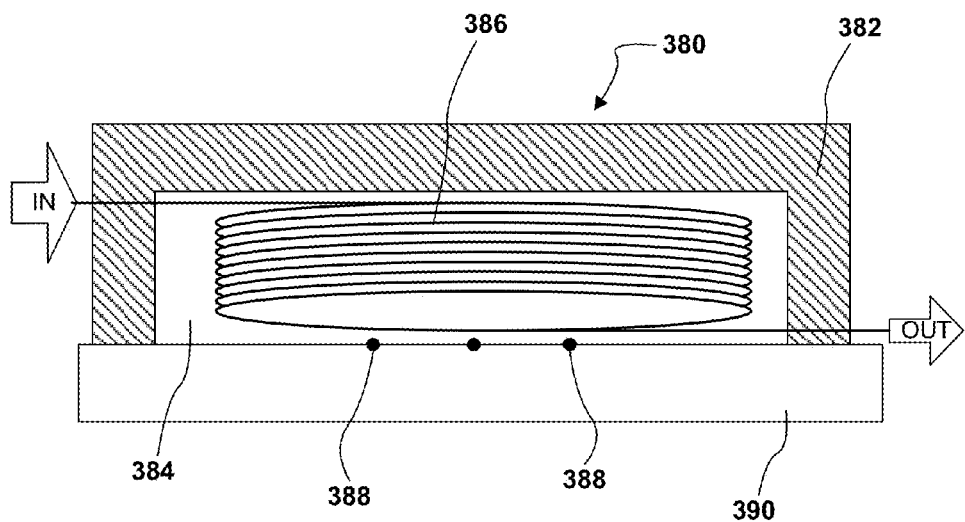
FIG. 3E is a cross-sectional elevation drawing of the embodiment of a gas chromatograph shown in FIG. 3D.

FIGS. 3D and 3E together illustrate an alternative embodiment of an individual gas chromatograph 380. The primary difference between gas chromatographs 380 and 350 is the formation in chromatograph 380 of a conventional chromatography column instead of a MEMS chromatography column. Gas chromatograph 380 includes a substrate 382 having a cavity or opening 384 therein. Positioned within cavity 384 is a chromatography column 386, which in one embodiment can be formed using coiled capillary tube used in conventional chromatography. In one embodiment the length of column 386 can be from 1-10 m, but in other embodiments it can be necessary to limit the length to 1-3 m because of the more bulky configuration. A temperature control 390 is bonded to substrate 382 to close cavity 384, thus enclosing column 386. In one embodiment, temperature control 390 can be an external temperature control as shown and described for FIG. 3C, and can include one or more temperature sensors 388 to monitor the temperature and/or provide feedback control of the temperature control. GC 380 can be packaged in a small size to achieve faster heating and cooling control.

Operation of gas chromatograph 380 is similar to gas chromatograph 350 shown in FIG. 3C. The primary difference between gas chromatographs 380 and 350 is the formation of chromatography column. Instead of using MEMS fabricated column chip, the column can be formed by coiled capillary tube used in conventional chromatography. The column is then enclosed by a temperature control 390 as shown in FIG. 3E. Such a GC can be packaged in a small size to achieve faster heating and cooling control.

Figure 4A:
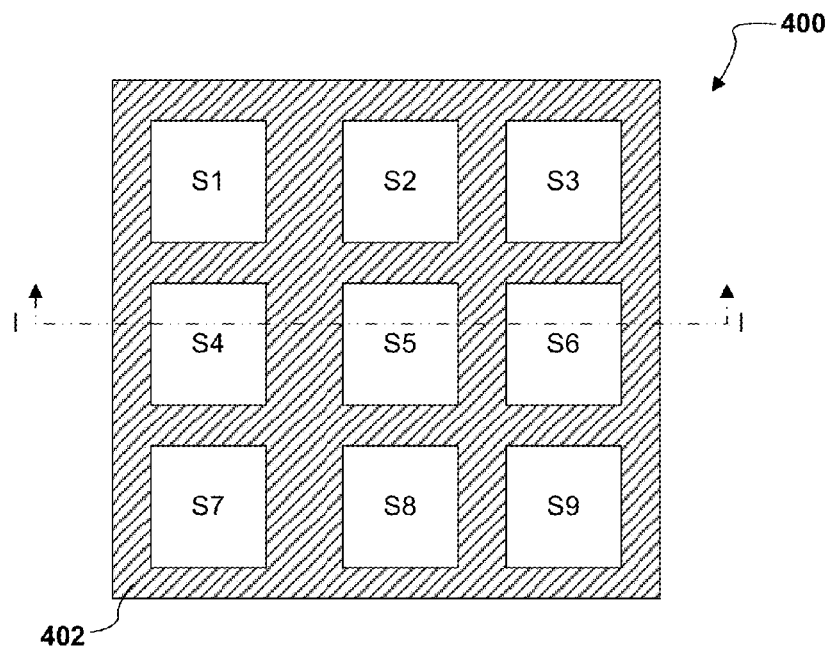
FIG. 4A is a plan view drawing of an embodiment of a detector array that can be used in the embodiment of a gas analysis device of FIGS. 1A-1B.
Figure 4B:
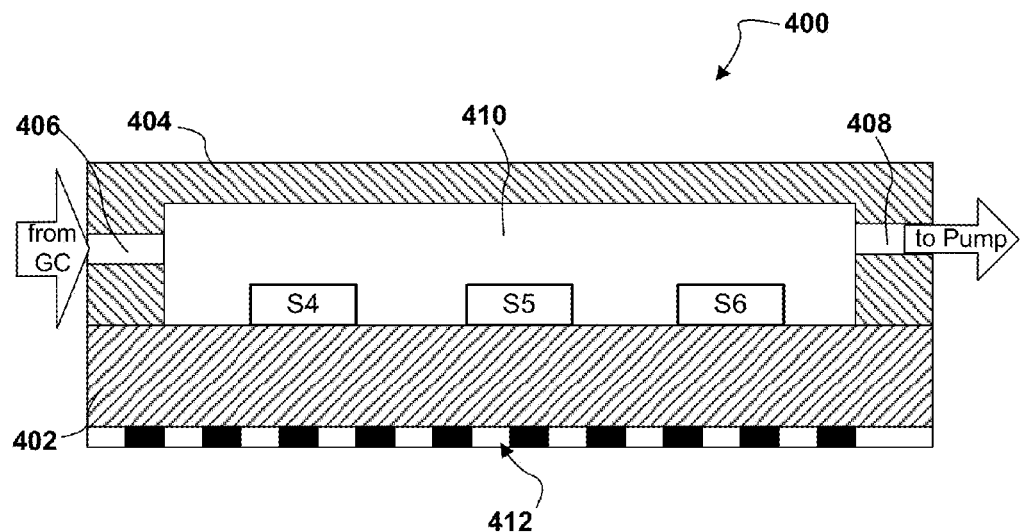
FIG. 4B is a cross-sectional elevation drawing of the embodiment of a detector array shown in FIG. 4A, taken substantially along section line I-I.

FIGS. 4A-4B illustrate an embodiment of a detector array 400 that can be used as detector array 110 in device 100. Detector array 400 includes a substrate 402 with an array of sensors S1-S9 formed thereon. In the illustrated embodiment sensors S1-S9 form a regularly shaped 3-by-3 array of sensors, but in other embodiments the sensor array can have a greater or lesser number of sensors, and the sensors can be arranged in any pattern, regular or irregular.

A cover 404 is bonded to the perimeter of substrate 402 to form a cavity 410 within which sensors S1-S9 are located. Cover 404 also includes an inlet 406 through which fluid can enter from gas chromatograph 108 and an outlet 408 through which fluid can exit to pump 112. A heater 412 is formed on the side of substrate 402 opposite the side where cover 404 is attached to control the temperature of detector array 400, and hence the sensors within the detector array, during operation. Although not shown in the Fig., detector array 400 of course includes outputs by which signals generated by sensors S1-S9 can be output for processing.

Each sensor S1-S9 includes a surface with a coating thereon. Each coating used will have an affinity for one or more of the particular chemicals being detected, such that the coating absorbs or chemically interacts with its corresponding chemical or chemicals. The interaction between coating and chemical in turn changes a physical property of the sensor such as resonant frequency, capacitance or electrical resistance, and that changed physical property of the sensor can be measured using a transducer or other measurement device. The particular coatings chosen for sensors S1-S9 will depend on the chemicals that sensor array 110 will be used to detect. The chemical affinity of coatings also varies strongly with temperature, so that the operating temperature range should be considered in selecting coatings. In an embodiment where sensor array 110 will be used to detect volatile organic compounds in human breath—such as benzene, toluene, n-octane, ethylbenzene, m,p-xylene, α-pinene, d-limonene, nonanal, and benzaldehyde, 2-methylhexane, 4-methyloctane, and so on—coatings that can be used in different applications include amorphous copolymers of 2,2-bistrifluoromethyl-4, 5-difluoro-1,3-dioxole (PDD) and tetrafluoroethylene (TFE), $PtCl_2$ (olefin), C8-MPN, etc.

Although the illustrated embodiment has nine sensors, the number of sensors needed depends on the number of different chemicals to be detected, and on the nature of the coatings used on the sensors. In an embodiment where each coating absorbs or chemically interacts with only one chemical the number of sensors can correspond exactly to the number of chemicals to be detected, but in other embodiments it can be desirable to have a given coating on more than one sensor for redundancy. In most cases, however, there is no one-to-one correlation between chemicals to coatings; in other words, each coating reacts with more than one different chemical and the reaction between different chemicals and a given coating will vary in nature and strength. A detector array having sensors with different coatings is therefore useful because the response of the detector array can have different patterns for different gases.

In one embodiment of sensor array 400, sensors S1-S9 are MEMS sensors positioned on the surface of substrate 402, meaning that they are surface micromachined sensors. In other embodiments using MEMS sensors, however, sensors S1-S9 can be bulk micromachined sensors, meaning that at least some of the MEMS sensors are formed within substrate 402 instead of on the surface. Still other embodiments of sensor array 110 using MEMS sensors can include combinations of surface-micromachined and bulk-micromachined sensors. Different types of MEMS sensors can be used, depending on the application and the required sensitivity. Examples of MEMS sensors that can be used include chemiresistors, bulk acoustic wave (BAW) sensors, etc. In other embodiments of detector array 400, one or more of sensors S1-S9 can be a non-MEMS sensor. Examples of non-MEMS sensors that can be used in detector array 400 include quartz crystal microbalance (QCM) or surface acoustic wave (SAW) sensors with quartz or gallium arsenide (GaAs) substrates.

During operation of MEMS detector array 400 in device 100, fluid from gas chromatograph 108 enters through inlet 406 and passes into cavity 410. Fluid entering cavity 410 carries time-domain separated chemicals. As each chemical enters cavity 410 it interacts with one or more sensors whose coating has an affinity for that chemical. The interaction of the chemical with the sensor is sensed and measured, and the presence and concentration of the particular chemical can be extracted. As more fluid flows into cavity 410, the first chemical is pushed out of cavity 410 through outlet 408 and fluid with the next time-domain-separated chemical enters cavity 410, interacts with the sensor array and is measured. This process continues until all the time-domain-separated chemicals from gas chromatograph 108 have flowed through detector array 110. In some embodiments where the affinity of the coatings for their chemicals is not strong, detector array 110 can be re-usable: after all time-domain-separated chemicals have been sensed, heater 412 can be activated to heat the sensors and cause the coatings to release the respective chemicals with which they interacted, making the interaction reversible. In embodiments where the affinity of each coating for its chemicals could be strong, heating of the sensor array could help release the partially absorbed gas from the coating materials.

Figure 4C:
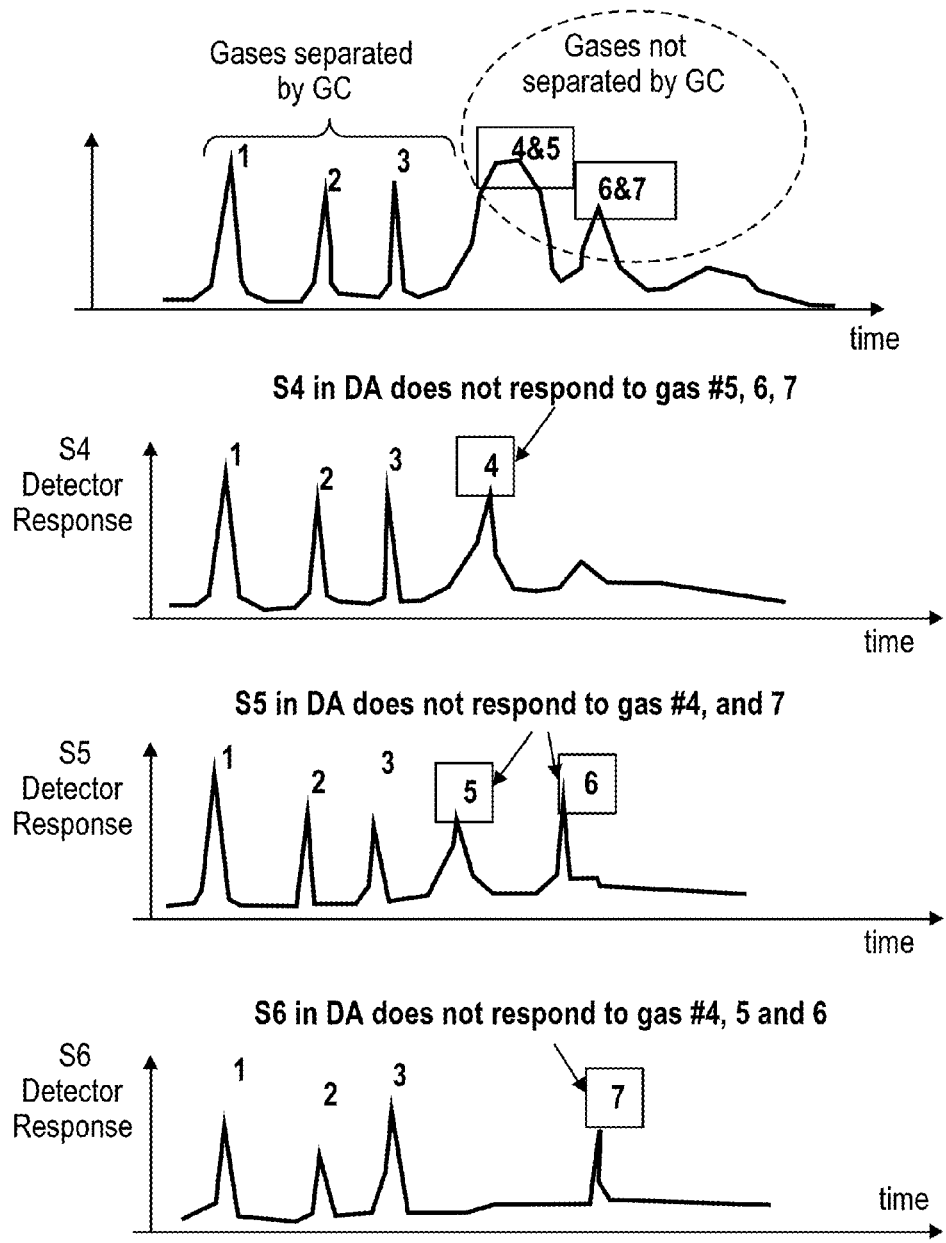
FIG. 4C is a set of graphs illustrating an embodiment of unseparated or partially separated chemicals and selective sensor responses to the partially separated chemicals.

FIG. 4C illustrates an alternative embodiment of the operation of detector array 400 in device 100. In this embodiment of operation, by choosing the chemical sensitivities of individual detectors S1-S9 detector array 400 can be used to detect analytes (e.g., chemicals such as gases or volatile organic compounds (VOCs)) that were either unseparated or not completely separated (e.g., partially separated) by GC 108. The top graph illustrates an example of the output of GC 108. In this example the fluid flowing through system 100 contains seven analytes, but GC 108 could not completely separate all seven: analytes 1-3 were completely separated by GC 108, as indicated by their narrow peaks on the graph, but analytes 4-5 could not be completely separated, nor could analytes 6-7, as indicated by their broad peaks in the graph. In such an example, it can nonetheless be possible to correctly detect analytes 4-7 by choosing individual detectors S1-S9 in detector array 400 to be selective to the analytes that GC 108 cannot separate or, put differently, to be unresponsive to analytes that are can be completely separated. For example, the second graph in FIG. 4C illustrates the response of detector S4 where detector S4 has been chosen to be unresponsive to analytes 5-7, so that detector S4 can detect analyte 4 even though it wasn't completely separated by GC 108. Similarly, the third graph in FIG. 4C illustrates the response of detector S5 where detector S5 has been chosen to be unresponsive to analytes 4 and 7, so that detector S5 can detect analytes 5 and 6 even though they weren't completely separated by GC 108. Finally, the last graph in FIG. 4C illustrates the response of detector S6 where detector S6 has been chosen to be unresponsive to analytes 4, 5 and 6, so that detector S6 can detect analyte 7 even though it wasn't completely separated by GC 108. In this way, GC 108 and detector array effectively cooperate to separate chemicals that cannot be separated by GC 108 alone.

Figure 5:
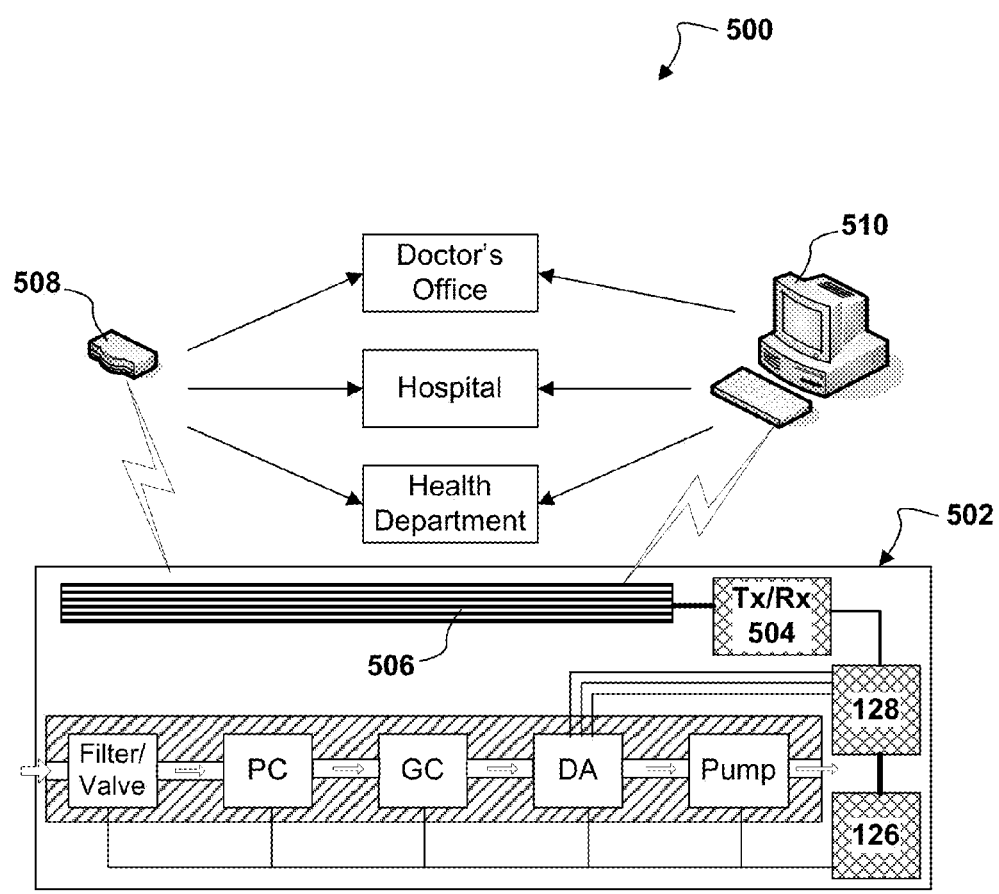
FIG. 5 is a schematic diagram of an alternative embodiment of a gas analysis device and an embodiment of a system using the embodiment of the gas analysis device.

FIG. 5 illustrates an embodiment of a system 500 using an alternative embodiment of a MEMS-based gas analysis device 502. Device 502 is in most respects similar to device 100. The primary difference between device 502 and device 100 is the presence in device 502 of a wireless transceiver circuit 504 and an antenna 506 mounted on substrate 102. Wireless transceiver circuit 504 can both transmit (Tx) data and receive (Rx) data and is coupled to reading and analysis circuit 128 and antenna 506.

In one embodiment of system 500, transceiver 504 can be used to wirelessly transmit raw data from reading and analysis circuit 128 to one or both of a router 508 and a computer 510. When transmitted to router 508, the data can then be re-transmitted to another destination for analysis. For example, in an application where device 502 is used for health-related chemical analysis, data sent to router 508 can be re-transmitted to one or more of a doctor's office, a hospital, a government health department, or someplace else for analysis and interpretation. After analysis is complete, or if there is a problem with the data, the doctor's office, hospital or health department can send instructions to device 502 through router 508, antenna 506 and transceiver 504 to signal the result, to try to fix or improve the data, or to signal that the test must be performed again.

Continuing with the same health-care example, in the same or another embodiment of system 500, wireless transceiver 504 can be used to transmit raw data to computer 510. Computer 510 can either forward the raw data to a doctor, hospital, etc., as did the router, or can analyze the data with software installed thereon to provide extract information from the data, such as one or more possible medical diagnoses, and provide the extracted information to the user of device 502. When it provides analysis and medical diagnoses, computer 510 can also forward the diagnosis, alone or with the analysis and raw data, on to the doctor, hospital, etc. As with the router, the doctor's office, hospital or health department can send instructions to device 502 through computer 510, antenna 506 and transceiver 504 to try to fix or improve the data, to signal that the test must be performed again, and so on.

Again continuing with the same health-care example, in still another embodiment of system 500 the raw data can be processed, and information such as potential diagnoses extracted from the data, by reading and analysis circuit 128. The potential diagnoses determined by reading and analysis circuit 128 can then be sent to computer 510 to be reviewed by the user and/or forwarded, or can be immediately forwarded alone or with the supporting raw data to the doctor's office, etc.

Figure 6:
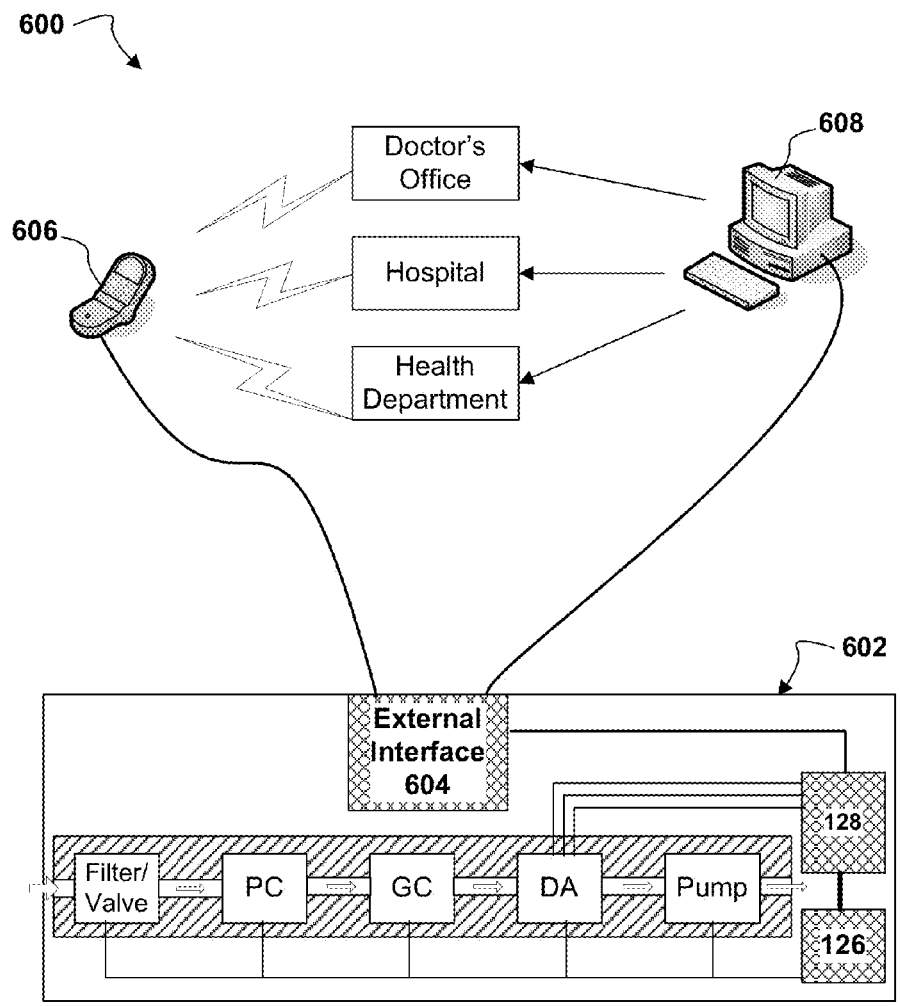
FIG. 6 is a schematic diagram of another alternative embodiment of a gas analysis device and an embodiment of a system using the embodiment of the gas analysis device.

FIG. 6 illustrates an embodiment of a system 600 using an alternative embodiment of a MEMS-based gas analysis device 602. Device 602 is in most respects similar to device 502. The primary difference between device 502 and device 602 is that the wireless transceiver circuit 504 and antenna 506 are replaced with a hardware data interface 604 coupled to reading and analysis circuit 128. In one embodiment, hardware data interface 604 could be a network interface card, but in other embodiments hardware data interface can be an Ethernet card, a simple cable plug, etc. External devices can be connected to device 602 through traditional means such as cables. Although it has a different communication interface, device 602 and system 600 have all the same functionality as device 502 and system 500. As with system 500, in system 600 MEMS-based gas analysis device 602 can transmit data to, and receive data from, one or both of a computer 608 and a wireless device 606, such as a cell phone or personal digital assistant (PDA). When transmitted to wireless device 606 the data can then be forwarded to a doctor's office, hospital, or government health department, and the recipients of the data can in turn send data or instructions back to gas analysis device 602 through the wireless device. As in system 500, when data is transmitted to computer 608 it can be forwarded or can be analyzed by the computer and the result displayed for the user and/or forwarded, and instructions can be transmitted to device 602 through computer 608. Similarly, the data from gas analysis device 602 can be analyzed by reading and analysis circuit 128. After analysis by circuit 128, the extracted information (e.g., one or more diagnoses) and/or the raw data can be forwarded via the hardware data interface 604.

Figure 7:
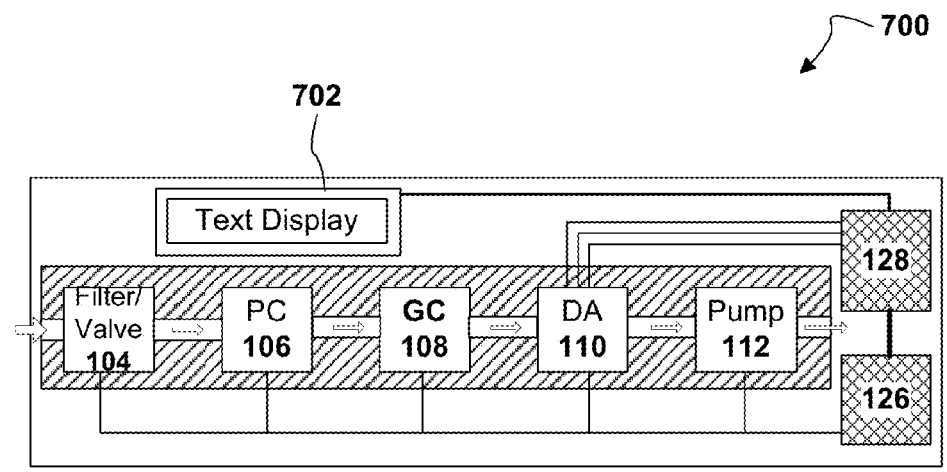
FIG. 7 is a plan-view schematic diagram of an additional alternative embodiment of a gas analysis device.

FIG. 7 illustrates an alternative embodiment of a MEMS-based gas analysis device 700. Device 700 is in most respects similar to device 100. The primary difference between system 700 and device 100 is that device 700 includes an on-board display 702 for conveying to a user the results of the analysis performed by reading and analysis circuit 128.

The illustrated embodiment uses an on-board text display 702, for example an LCD screen that can convey text information to a user. For example, in a health care example display 702 could be used to display the test results in analog numbers indicating the situation of patients. Display 702 could indicate a positive or negative diagnosis, could indicate probabilities of a given diagnosis, or could indicate the raw data from the detector array. In another health care embodiment, simpler displays can be used, such as one with three lights that indicate a positive, negative, or indeterminate result depending on which light is switched on.

Figure 8:
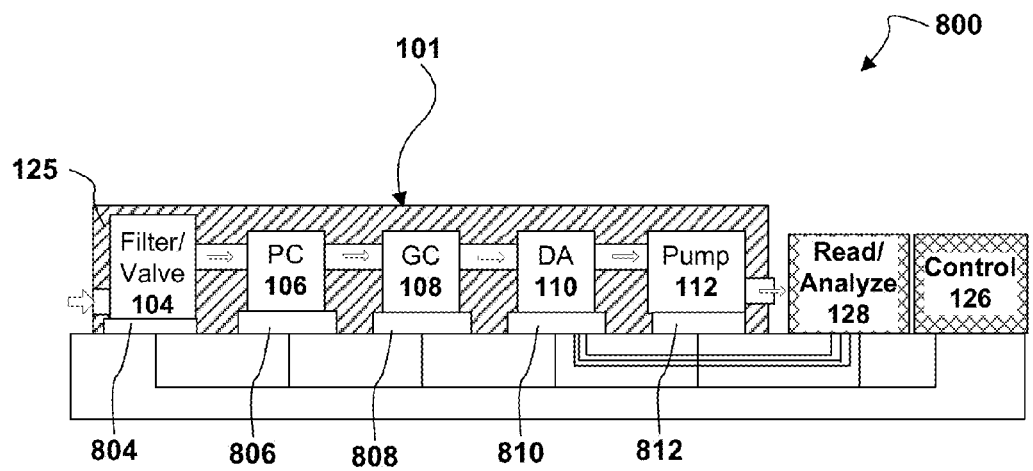
FIG. 8 is a side elevation schematic diagram of an additional alternative embodiment of a gas analysis device.

FIG. 8 illustrates an alternative embodiment of a MEMS-based gas analysis device 800. Device 800 is in most respects similar to device 100. The primary difference between device 800 and device 100 is that in device 800 one or more elements of fluid handling assembly 101 are replaceable. In the illustrated embodiment, the elements are made replaceable by mounting them onto substrate 102 using sockets: filter and valve assembly 104 is mounted to substrate 102 by socket 804, pre-concentrator 106 is mounted to substrate 102 by socket 806, gas chromatograph 108 is mounted to substrate 102 by socket 808, detector array 110 is mounted to substrate 102 by socket 810, and pump 112 is mounted to substrate 102 by socket 812. In one embodiment, sockets 804-812 are sockets, such as zero insertion force (ZIF) sockets, that permit easy replacement by a user, but in other embodiments other types of sockets can be used. Although the illustrated embodiment shows all the components of fluid handling assembly 101 being replaceable, in other embodiments only some of the components such as pump 112 and detector array 110 can be made replaceable.

Figure 9:
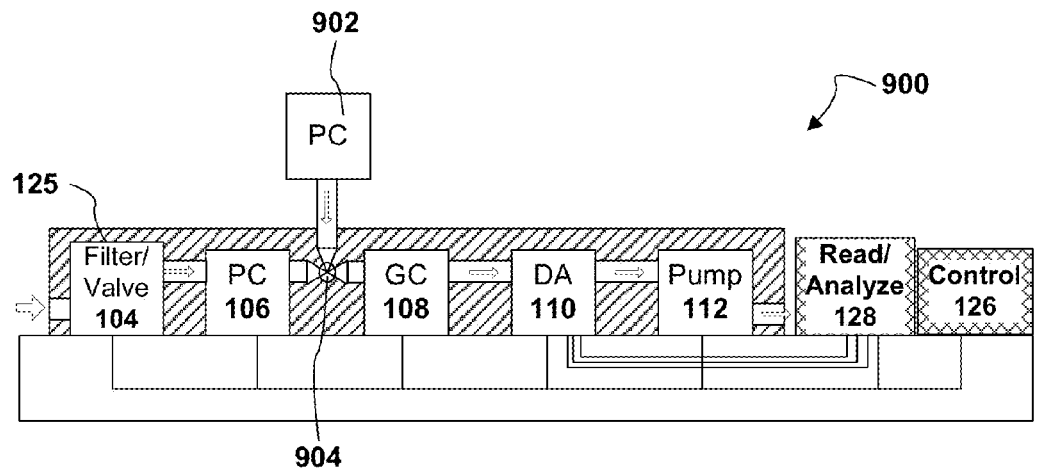
FIG. 9 is a side elevation schematic diagram of an additional alternative embodiment of a gas analysis device.

FIG. 9 illustrates an alternative embodiment of a MEMS-based gas analysis device 900. Gas analysis device 900 is in most respects similar to device 100. The primary difference between device 900 and device 100 is that device 900 includes provisions for an external pre-concentrator 902 (i.e., a pre-concentrator not mounted on substrate 102). In the embodiment shown, a valve 904 is placed between pre-concentrator 106 and gas chromatograph 108, and provisions are made to attach external pre-concentrator 902 to the valve. Valve 904 allows the user to use external pre-concentrator 902 instead of, or in addition to, on-board pre-concentrator 106. In one embodiment external pre-concentrator 902 is a breath collection bag, but in other embodiments it can be something different. In an alternative embodiment of device 900 (not shown), pre-concentrator 106 can be permanently removed and replaced by external pre-concentrator 902. In another embodiment where external pre-concentrator 902 replaces pre-concentrator 106, instead of inserting a valve between pre-concentrator 106 and gas chromatograph 108, external pre-concentrator 902 can be coupled upstream of the filter and valve assembly 104.

Figure 9A:
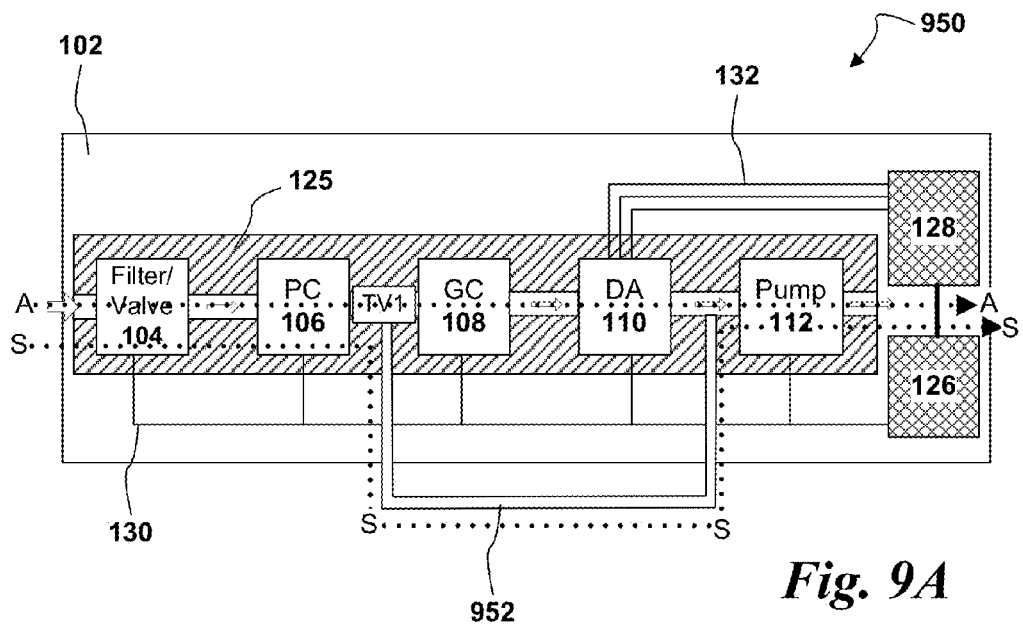
FIG. 9A is a plan-view schematic of a further additional alternative embodiment of a gas analysis device.

FIG. 9A illustrates a further alternative embodiment of a gas analysis device 950. Gas analysis device 950 is in most respects similar to device 100. The primary difference between device 950 and device 100 is that device 950 includes a three-way valve TV1 in the fluid connection between pre-concentrator 106 and gas chromatograph (GC) 108, as well as a fluid connection 952 that couples three-way valve TV1 to the fluid connection between detector array (DA) 110 and pump 112. Three-way valve TV1 and fluid connection 952 provide device 950 with different fluid paths for different operation modes.

When device 950 is operated in sampling mode (e.g., collecting a breath sample for analysis), three-way valve TV1 is set so that the fluid flows through device 950 along the flow path shown with the dotted line labeled S. In sampling mode, fluid enters device 950 and passes through filter/valve 104 and through pre-concentrator 106. Following the pre-concentrator, three-way valve TV1 diverts the flow into fluid connection 952 so that the flow bypasses GC 108 and DA 110 and goes into the inlet of pump 112, which then exhausts the fluid to the atmosphere. When device 950 is operated in analysis mode (e.g., when separating analytes such as VOCs), three-way valve TV1 is set so that the fluid flows through device 950 along the flow path shown with the dotted line labeled A. In analysis mode, fluid enters device 950 and passes through filter/valve 104 and through pre-concentrator 106. Following the pre-concentrator, three-way valve TV1 is set to direct the flow into GC 108 instead of fluid connection 952. After passing through GC 108, the flow continues into DA 110 for analysis and then goes into pump 112, after which it is exhausted to the atmosphere.

Figure 9B:
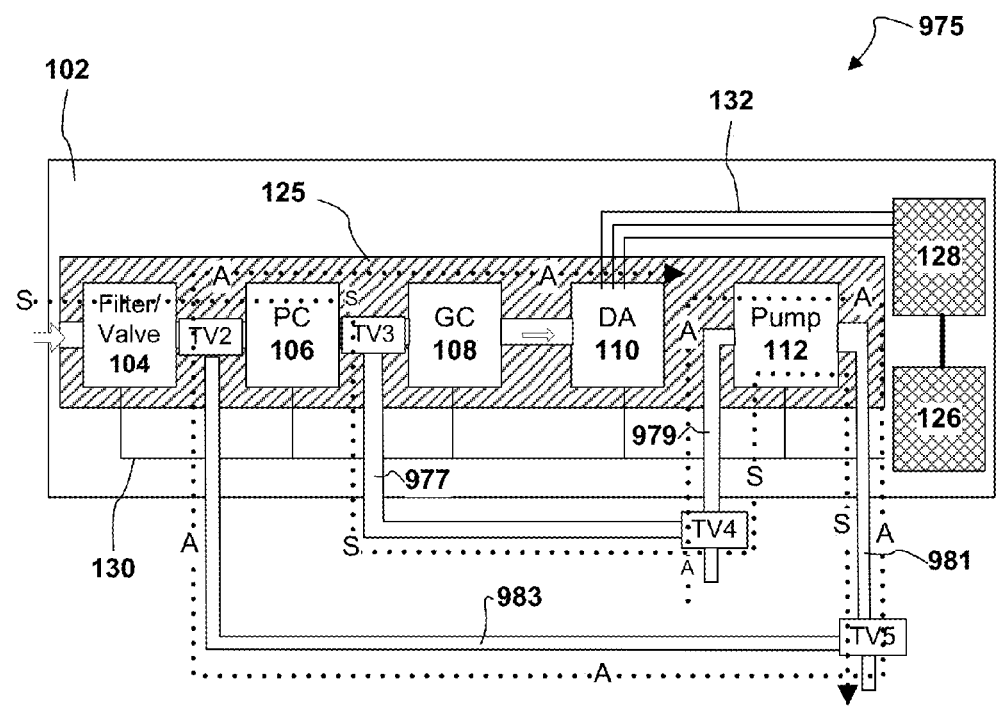
FIG. 9B is a plan-view schematic of a further additional alternative embodiment of a gas analysis device.

FIG. 9B illustrates a further alternative embodiment of a gas analysis device 975. Gas analysis device 975 is in most respects similar to device 100. The primary difference between device 975 and device 100 is that device 975 includes additional elements to provide different fluid paths for different operation modes. Device 975 includes a first three-way valve TV2 in the fluid connection between filter/valve unit 104 and pre-concentrator 106, as well as a second three-way valve TV3 in the fluid connection between PC 106 and gas chromatograph (GC) 108. A fluid connection 977 couples second three-way valve TV3 to a third three-way valve TV4, which is in turn coupled to the inlet of pump 112 by fluid connection 979. Similarly, a fluid connection 983 couples first three-way valve TV2 to a fourth three-way valve TV5, and fourth three-way valve TV5 is in turn coupled to the outlet of pump 112 by fluid connection 981.

When device 975 is operated in sampling mode (e.g., collecting a breath sample for analysis), three-way valves TV2-TV5 are set so that the fluid flows through device 975 along the flow path shown with the dotted line labeled S. In sampling mode, fluid enters device 975 and passes through filter/valve 104 and pre-concentrator 106. Following pre-concentrator 106, three-way valve TV3 diverts the flow into fluid connection 977, so that the flow bypasses GC 108 and DA 110 and goes to three-way valve TV4. Three-way valve TV4 is set so that it directs the flow to the inlet of pump 112, which then exhausts the fluid into fluid connection 981. Fluid connection 981 directs the fluid from pump 112 to three-way valve TV5, which is set to exhaust the fluid to the atmosphere. When device 975 is operated in analysis mode (e.g., when separating analytes such as VOCs), three-way valves TV2-TV5 are set so that the fluid flows through device 975 along the flow path shown with the dotted line labeled A. In analysis mode, pump 112 draws fluid from the atmosphere into device 975 through three-way valve TV4 and fluid connection 979. Fluid connection 981 is coupled to the outlet of pump 112 and carries the fluid to three-way valve TV5, which is set to direct the fluid into fluid connection 983. Fluid connection 983 then carries the fluid to three-way valve TV2, which is set to direct the fluid to the inlet of PC 106. Three-way valve TV3 is set so that fluid exiting PC 106 is directed into GC 108, then into DA 110, and then into the atmosphere.

Figure 10:
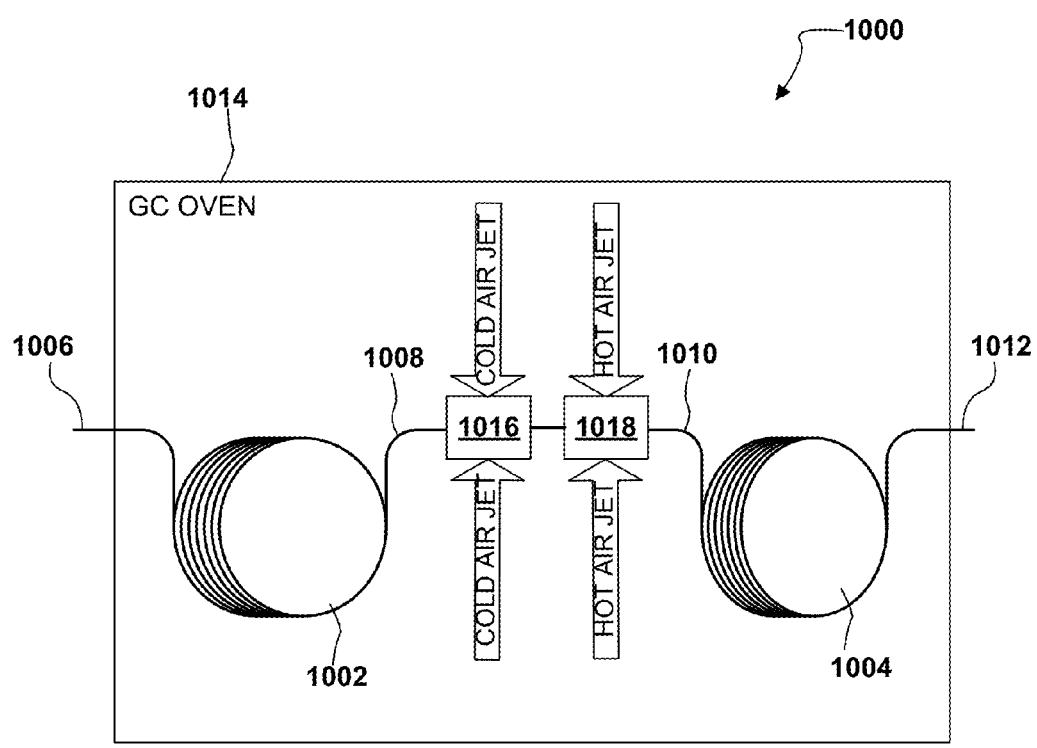
FIG. 10 is a schematic of an embodiment of cascaded gas chromatographs with spectrum sharpening.

FIG. 10 illustrates an embodiment of a cascaded gas chromatograph (CGC) 1000 using analyte focusing. CGC 1000 includes a first gas chromatograph (GC) 1002 having a fluid inlet 1006 and a fluid outlet 1008. A second GC 1004 has a fluid inlet 1010 and a fluid outlet 1012, with the fluid inlet 1010 coupled to the fluid outlet 1008 by a fluid connection. Surrounding the fluid connection between GC 1002 and GC 1004 are a cooling section 1016 and a heating section 1018. The entire assembly is positioned within a GC oven 1014.

In operation of CGC 1000, a carrier gas including one or more chemicals (also known as an analytes) enters first GC 1002 through its fluid inlet 1006. After the analytes circulates through GC 1002, they exit the GC through fluid outlet 1008 and flow in the fluid connection through cooling section 1016, where a cold air jet is directed into the cooling section to cool the analytes. The cold air used in cooling section 1016 can be produced using either liquid nitrogen or dry ice. After flowing in the fluid connection through cooling section 1016, the analytes continue into heating section 1018. In heating section 1018, a hot air jet is used to heat the previously cooled analytes. Following heating section 1018, the analytes proceed through fluid inlet 1010 to enter GC 1004 for further separation. CGC 1000 is bulky and expensive, and therefore cannot be used as portable gas analysis systems. Moreover, only a small section of CGC 1000 can be cooled due to its large thermal mass.

FIGS. 11A-11B illustrate an embodiment of focusing analytes (such as volatile organic compounds (VOCs) by cooling and/or heating a GC. In each figure, the lower graph illustrates a temperature profile (e.g., a variation of temperature with time) that is applied to a GC, while the upper graph illustrates the response of a detector coupled to that GC. FIG. 11A illustrates an approach in which the GC begins at an initial temperature that is then ramped up to a target temperature at a desired ramping rate. With this temperature profile, gases 1, 2 and 3, are separated, but other gases remain unseparated by the GC. In most situations, the input analytes/VOCs have a broad concentration distribution when entering the GC column. The spectrum becomes wider and lower as analytes are traveling within the GC column while separating from each other in time at output of GC. In most situations, some of the analyte spectrums are too wide and overlap with each other, which results in non-separated gases as show in the figure.

FIG. 11B illustrates an alternative approach. The temperature profile is shown in the bottom graph: the temperature of the chromatograph begins at initial temperature and is then cooled (reduced or lowered) to a lower temperature. After reaching the lowest temperature desired, the cooling is followed by heating the chromatograph to an operating temperature. The results of applying the temperature profile shown in the lower graph are shown in the detector response graph. The same gases 1-3 are separated from the analyte, but because of the focusing effect of cooling the analyte, gases that were previously un-separated are now separated, as shown by the sharp peaks in the detector response. The cooling produces an immediate focusing effect and narrowing (sharpening) of the spectrum profile. The micro-GC is then heated to targeted temperature with the desired ramping rate to achieve analyte/VOC separation. Due to the operation of micro-GC cooling, the output spectrums are sharper compared to non-cooling operation. With sharper spectrums, gases/VOCs overlap at the micro-GC output will be reduced. As a result, more analytes can be resolved with micro-GC cooling.

FIG. 11C illustrates an embodiment of a temperature profile that can be applied to a GC to obtain analyte focusing. For purposes of this application, the term "temperature profile" refers to a variation of temperature with time. In FIG. 11C, the vertical axis represents a temperature of the GC, while the horizontal axis represents time.

Prior to time $t_0$, the GC is maintained at an initial temperature T0. In one embodiment, initial temperature T0 is substantially room temperature (typically around 20° C., but not limited to this temperature), but in other embodiments the initial temperature can be a temperature lower or higher than room temperature. Starting at time $t_0$, the profile begins a first time period from time $t_0$ until time $t_1$ during which the temperature of the GC is lowered (i.e., the GC is cooled) until it reaches a temperature T1 lower than the initial temperature T0. In one embodiment temperature T1 is a temperature below freezing, for example −10° C., but in other embodiments T1 can be any temperature lower than initial temperature T0. In one embodiment the duration of the first period $(t_1-t_0)$ can be from 2-10 seconds, but in other embodiments the first period can be shorter or longer. Moreover, although the illustrated embodiment shows the temperature decreasing linearly in the first period, in other embodiments the temperature decrease in the first period need not be linear.

At the end of the first period, after reaching temperature T1 at time $t_1$, the temperature profile enters a second period from time $t_1$ to time $t_2$ during which the temperature of the GC is held substantially at or about T1. In one embodiment the duration of the second period $(t_2-t_1)$ can last from a few seconds to a couple of minutes, but in other embodiments the duration of the second period can be essentially zero, such that $t_2=t_1$. At the end of the second period at time $t_2$, the temperature profile enters a third period from time $t_2$ to time $t_3$ during which the GC temperature is increased from T1 to a target temperature T2. In one embodiment T2 can be about +80° C., but in other embodiments other target temperatures are possible. In one embodiment the duration of the third period $(t_3-t_2)$ can be from 2-10 seconds, but in other embodiments the third period can be shorter or longer. Moreover, the illustrated embodiment shows the temperature increasing linearly at the beginning of the third period and then increasing more slowly and non-linearly until the temperature reaches T2, but in other embodiments other distributions of temperature with time are possible. For example, in one embodiment the temperature increase during the third period can be completely linear from $t_2$ to $t_3$. In another example, the temperature of the gas chromatograph can initially overshoot temperature T2 and then be cooled to return the temperature to T2.

Figure 12A:
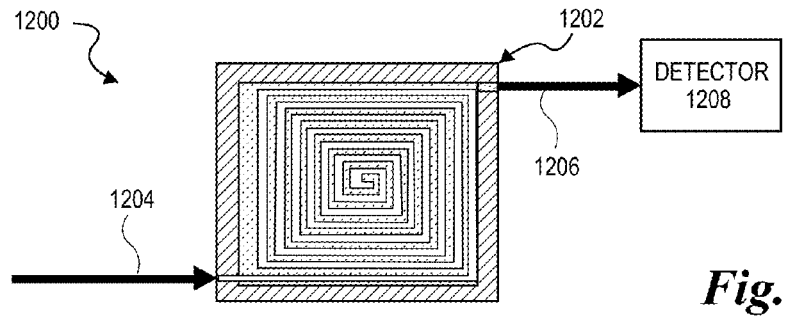
FIG. 12A is a schematic of an embodiment of a gas chromatograph.
Figure 12B:
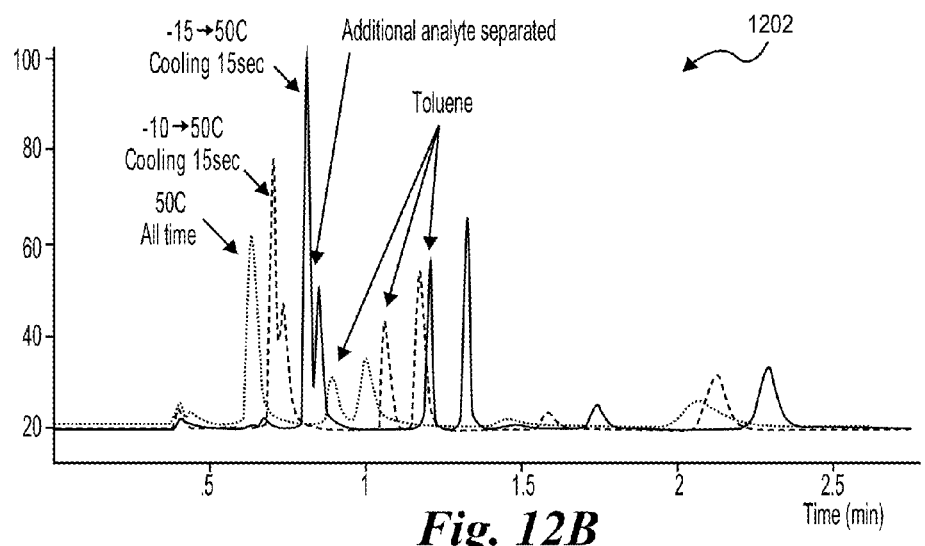
FIGS. 12B-12C are graphs of detector response to various embodiments of temperature profiles applied to the embodiments of a gas chromatographs shown in FIG. 12A.
Figure 12C:
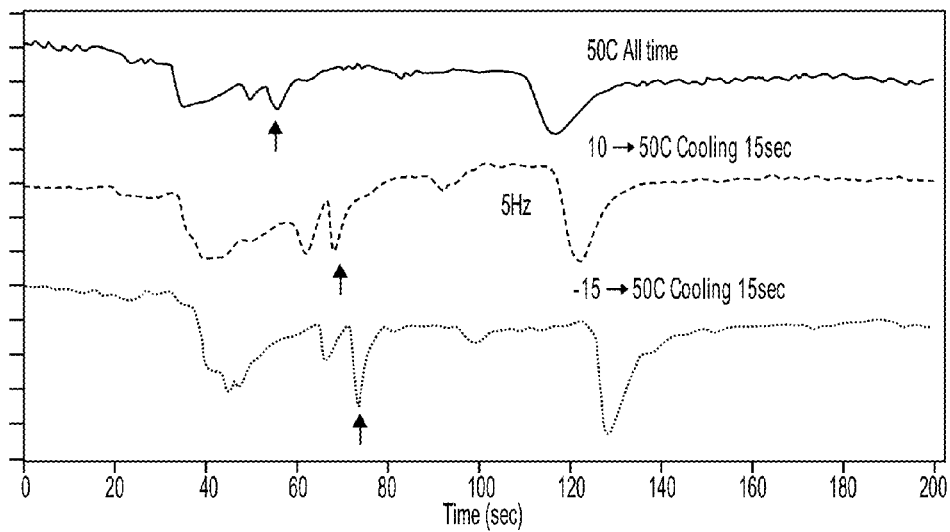

FIGS. 12A-12C illustrate the construction and operation of an embodiment of a system 1200. System 1200 includes a GC 1202 having a fluid inlet 1204 and a fluid outlet 1206. A detector 1208 is coupled to the fluid outlet 1206 by a fluid connection. GC 1202 includes a temperature control that allows the GC to be heated, cooled, or both heated and cooled, for example by using a temperature profile such as the one illustrated in FIG. 11C. In one embodiment, GC 1202 can have the construction illustrated in FIG. 3B-3C, but in other embodiments it can have a different construction, such as the one shown in FIGS. 3D-3E or some other construction altogether. Detector 1208 can be any kind of chemical detector; in one embodiment, it can be a detector array such as detector array 400 shown in FIGS. 4A-4B, but in other embodiments other kinds of detector arrays can be used. Although not shown in the figure, the temperature control of gas chromatograph 1202 can be coupled to a control circuit (such as control circuit 126 when chromatograph 1202 is used in gas analysis systems such as the ones shown in FIGS. 1A-1B and 5-9) that applies the temperature profile to the temperature control.

FIGS. 12B-12C illustrates the results obtained with system 1200 when temperature profiles such as the one shown in FIGS. 11A-11C are applied to GC 1200 and when a flame ionization detector (FID) is used (FIG. 12B) or when an acoustic resonator detector such as a surface acoustic wave (SAW) or QCM detector (FIG. 12C). Both figures show the results of applying three temperature profiles to GC 1202: a first temperature profile in which the temperature is kept at a constant 50C, a second temperature profile in which the temperature is reduced to 10° C., held for 15 seconds, and then increased to 50 C, and a third temperature profile in which the temperature is reduced to −15 C, held for 15 seconds, and then increased to 50 C. The results obtained from both detectors show significant improvement in VOC (analyte) spectrum sharpening (narrower and higher peaks). The lower the cooling temperature that is applied, the better the sharpening of the spectrum. With an increase on the spectrum height, the detector's detection limit can be improved. Meanwhile, with a narrower VOC spectrum, additional VOCs can be resolved (separated) from neighboring VOCs.

FIGS. 13A-13C illustrate the construction and operation of a cascaded gas chromatograph (CGC) 1300. Embodiments of CGC 1300 can be used in place of, or one or more of its components can be used to supplement, gas chromatograph (GC) 108 and detector 110 in gas analysis systems such as the ones shown in FIGS. 1A-1B and 5-9. CGC 1300 includes a first gas chromatograph (GC) 1302 coupled to a second GC 1304. In the illustrated embodiment, GCs 1302 and 1304 are coupled in series such that outlet 1308 of GC 1302 is coupled to inlet 1310 of GC 1304 by a fluid connection 1314. Outlet 1312 of GC 1304 is coupled to a detector 1318 by a fluid connection 1316, although in other embodiments outlet 1312 could be coupled to some entirely different component. Although the illustrated embodiment has only two GCs, in other embodiments one or more additional GCs, as well as other components such as additional fluid connections, flow splitters, three-way valves detectors and switch valves, can be added to form a larger cascade of GCs.

In the illustrated embodiment, GCs 1302 and 1304 are MEMS GCs with individual temperature controls, such as those shown in FIG. 3B or 3C, but in other embodiments they can be the capillary column GCs shown in FIGS. 3D-3E or some other construction altogether. The individual temperature controls allow the operating temperature of each GC to be controlled independently of the other. In other embodiments GCs 1302 and 1304 need not be of the same type—that is, CGC 1300 can include both MEMS and non-MEMS chromatographs. In some embodiments both chromatographs can have the same kind of temperature control, but in other embodiments both chromatographs need not have the same temperature control; for example, in the illustrated embodiment with two MEMS chromatographs, GC 1302 can have an integrated temperature control as shown in FIG. 3B, while GC 1304 has an external temperature control, as shown in FIGS. 3C-3E. In one embodiment, detector 1318 is a detector array as shown in FIGS. 4A-4B, but in other embodiments it can be a different type of detector. Although not shown in the figure, the temperature control of GCs 1302 and 1304 can be coupled to a control circuit (such as control circuit 126 when CGC 1300 is used in gas analysis systems such as the ones shown in FIGS. 1A-1B and 5-9) that applies a temperature profile to the temperature control. Because the temperature controls of GCs 1302 and 1304 are independent, in some embodiments different temperature profiles can be applied to each GC.

In some embodiments, GCs 1302 and 1304 can have the same characteristics, but in other embodiments GCs 1302 and 1304 need not have the same characteristics and can have different column lengths, column coatings, operating temperatures, etc. In one embodiment, for example, GC 1302 can be coated with material A, which can be especially selective to polar or non-polar chemicals, and can have its optimum temperature control profile to separate specific chemicals. Meanwhile, GC 1304 can have a different column length and can be coated with another material B, which can separate different chemicals that GC 1302 cannot resolve (separate); in other words, GC 1304 is complementary to GC 1302. Since each GC in the configuration can has its own temperature control, GC 1304 can be optimized to separate the remaining gases of interest that are not resolved (separated) by GC 1302. The separated gases can then be detected by detector 1318 at output of GC 1304.

In operation of CGC 1300, a carrier fluid having one or more chemicals therein enters GC 1302 through inlet 1306 and flows through the GC's column while a temperature profile from FIG. 11C or 13B is applied to the GC's temperature control. The carrier fluid, with any chemicals not resolved (separated) by GC 1302, exits through outlet 1308 into fluid connection 1314. Fluid connection 1314 carries the fluid into GC 1304, where the fluid flows through the GC's column while a temperature profile from FIG. 11C or 13C, which can be the same or different than the profile applied to GC 1302, is applied to the temperature control of GC 1304. As a result, some or all of the unresolved chemicals remaining after GC 1302 are separated. Outlet 1312 of GC 1304 is coupled to a detector 1318, which can then be used to detect the chemicals separated from the carrier fluid by the two GCs.

Figure 14B:
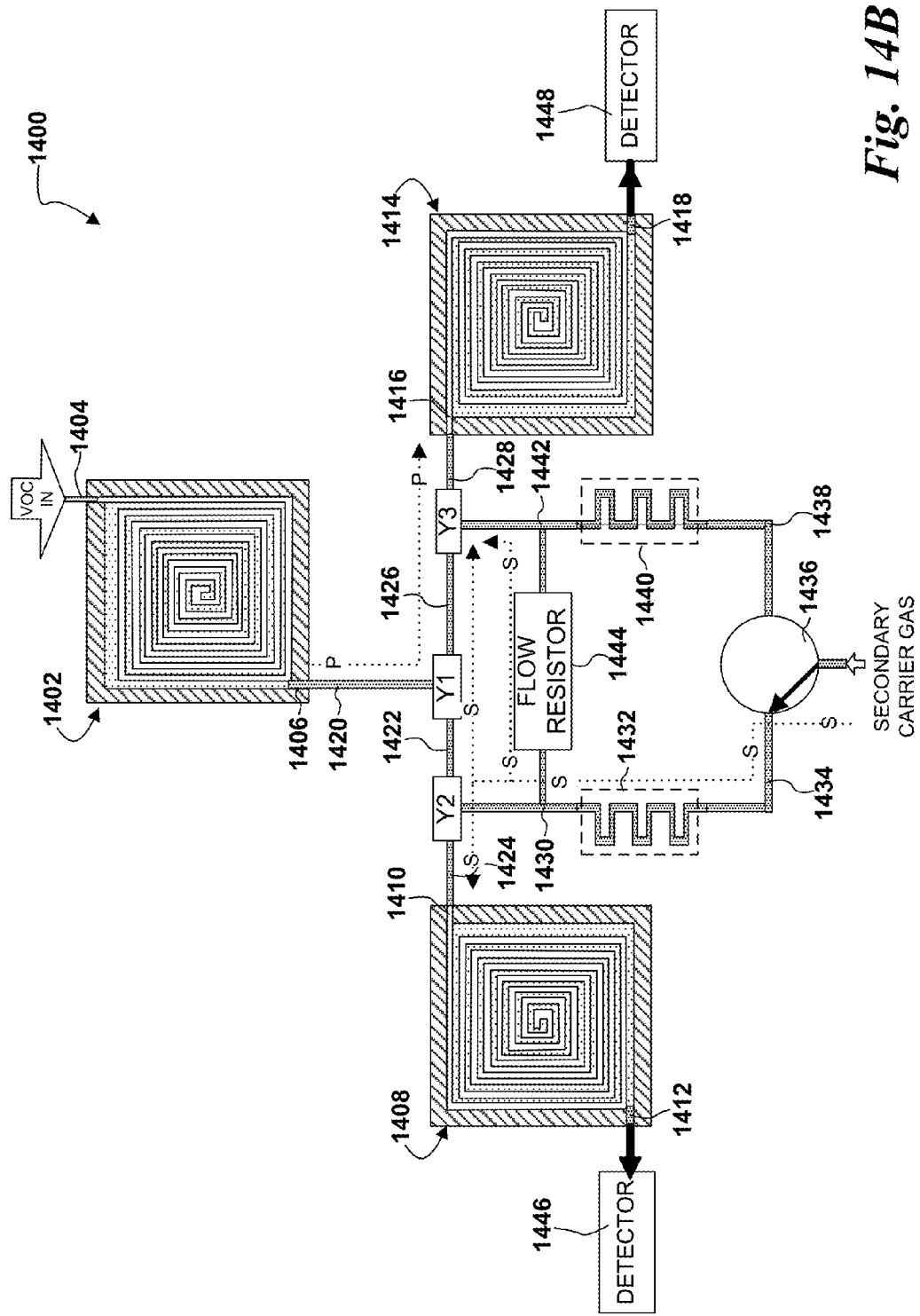

FIGS. 14A-14B together illustrate the construction and operation of an embodiment of a multi-dimensional gas chromatograph 1400. Embodiments of gas chromatograph 1400 can be used in place of, or one or more of its components can be used to supplement, gas chromatograph (GC) 108 and/or detector 110 in gas analysis systems such as the ones shown in FIGS. 1A-1B and 5-9.

Multi-dimensional gas chromatograph 1400 includes a first gas chromatograph (GC) 1402, a second GC 1408 and a third GC 1414 fluidly coupled to each other by several components that together form a "Dean switch." Each of the first, second and third GCs has its own temperature control that is independent of the others. In one embodiment, the first, second and third GCs can have the construction illustrated in FIGS. 3A-3C, but in other embodiments they can have a different construction, such as the one shown in FIGS. 3D-3E or some other construction altogether. In still other embodiments the first, second and third gas chromatographs need not have the same construction. As in CGC 1300, in some embodiments GCs 1402, 1408 and 1414 can have the same characteristics, but in other embodiments the individual GCs need not have the same characteristics and can have different column lengths, column coatings, operating temperatures, etc. Although not shown in the figure, the temperature controls of GCs 1402, 1408 and 1414 can be coupled to a controller or control circuit (such as control circuit 126 when multi-dimensional chromatograph 1400 is used in gas analysis systems such as the ones shown in FIGS. 1A-1B and 5-9) that applies temperature profiles to the temperature controls of the individual GCs during operation.

First GC 1402 includes a fluid inlet 1404 through which the analytes (e.g., volatile organic compounds (VOCs)) enter the GC and a fluid outlet 1406 through which separated chemicals exit GC 1402. Fluid outlet 1406 is coupled by fluid connection 1420 to a first Y-splitter Y1. First Y splitter Y1 is coupled to second Y-splitter Y2 by fluid connection 1422 and to third Y-splitter Y3 by fluid connection 1426. Second Y-splitter Y2 is further fluidly coupled to fluid inlet 1410 of second GC 1408 by fluid connection 1424, and fluid outlet 1412 of GC 1408 is coupled to a detector 1446. Similarly, third Y-splitter Y3 is coupled to fluid inlet 1416 of GC 1414 by fluid connection 1428, and fluid outlet 1418 of GC 1414 is coupled to a detector 1448. Second Y-splitter Y2 is coupled by secondary fluid connection 1430 to flow rate restrictor 1432, and flow-rate restrictor 1432 is coupled by fluid connection 1434 to a three-way valve 1436. Similarly, third Y-splitter Y3 is coupled by secondary fluid connection 1442 to flow rate restrictor 1440, and flow-rate restrictor 1440 is coupled by fluid connection 1438 to three-way valve 1436. Three-way valve 1436 is also coupled to a source of a secondary carrier gas. A flow resistor 1444 can optionally be fluidly coupled between fluid connections 1430 and 1442. The group of elements including the Y-splitters, the flow rate restrictors, the flow resistor, and the fluid connections among them together form a "Dean switch." Use of the Dean switch permits the use of "heart-cutting." In the heart-cutting technique, one or more unresolved (i.e., un-separated) analytes from a first chromatograph (first dimension) are transferred to one or more additional chromatographs having a different polarity (second dimension) where the separation of the compounds un-separated by the first chromatograph will be achieved.

In operation of multi-dimensional gas chromatograph 1400, the carrier gas containing chemicals (analytes) is directed into fluid inlet 1404 of GC 1404. Separated and unseparated analytes exit through fluid connection 1420 to Y-splitter Y1. At the same time, three-way valve 1436 is set to direct a secondary carrier gas into fluid connection 1438, so that the secondary carrier gas will flow through flow rate restrictor 1440 to Y-splitter Y3, where a portion of the secondary gas will flow into third GC 1414 and the remaining portion will flow through Y-splitters Y1 and Y2 into second GC 1408. When flow resistor 1444 is present, part of the secondary gas flows though the flow resistor. The path taken by the secondary carrier gas is illustrated by the dotted line labeled S. As a result of the flow of secondary carrier gas, the primary flow path, which carries analytes exiting from first GC 1402, is directed into second GC 1408, as shown by the dotted line labeled P. FIG. 14B illustrates another mode of operation of multi-dimensional GC 1400 in which flow is directed into third GC 1414 instead of second GC 1408 by switching three-way valve 1436 to its other position, such that the flow path S of the secondary carrier gas now changes the primary path P. During operation, temperature profiles are applied to the individual GCs to improve separation of the analytes. Because the temperature controls of GCs are independent, in some embodiments different temperature profiles can be applied to each GC.

Figure 15:
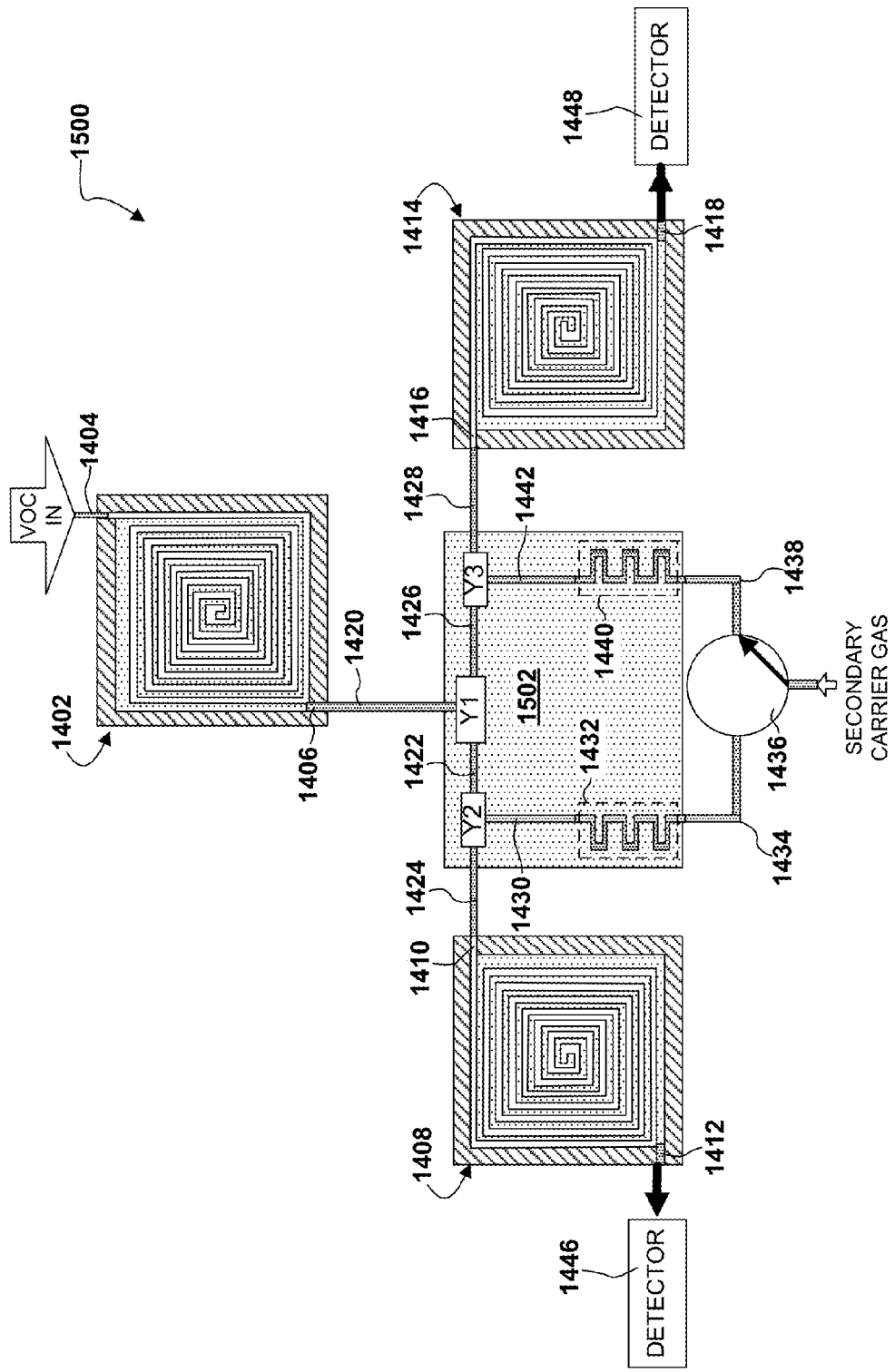
FIG. 15 is a schematic of an alternative embodiment of a multi-dimensional gas chromatograph.

FIG. 15 illustrates an alternative embodiment of a multi-dimensional gas chromatograph 1500. Embodiments of gas chromatograph 1500 can be used in place of, or one or more of its components can be used to supplement, gas chromatograph (GC) 108 and/or detector 110 in gas analysis systems such as the ones shown in FIGS. 1A-1B and 5-9. Multi-dimensional chromatograph 1500 is in most respects similar to multi-dimensional chromatograph 1400. The primary difference between chromatographs 1400 and 1500 is that in chromatograph 1500 elements of the Dean switch are formed on a microchip 1502. In the illustrated embodiment, Y-splitters Y1, Y2 and Y3 are formed on chip 1502 along with flow rate restrictors 1432 and 1440 and fluid connections between these elements. In other embodiments, additional elements such as flow resistor 1444 can also be formed on chip 1502.

Figure 16:
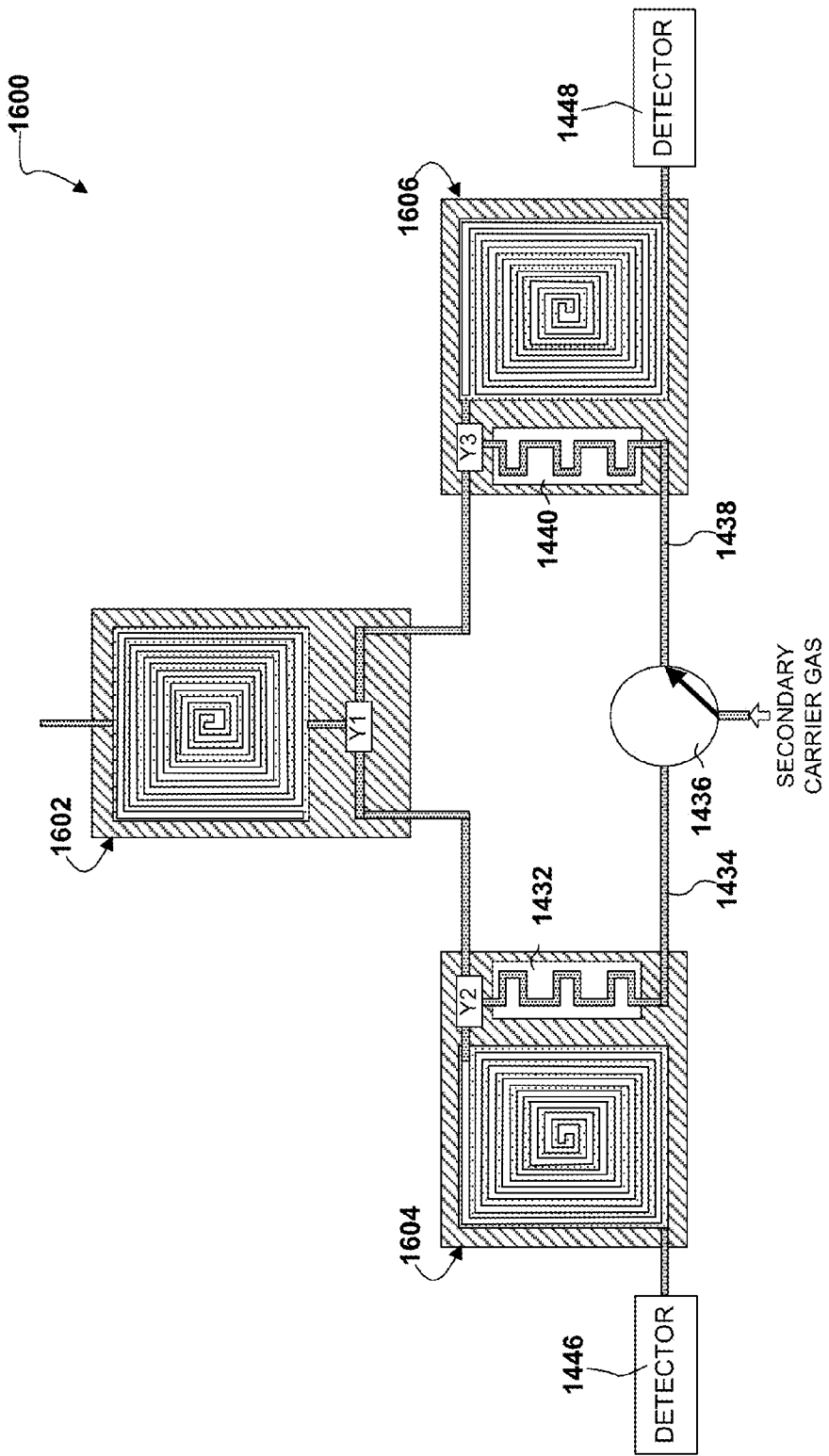
FIG. 16 is a schematic of another alternative embodiment of a multi-dimensional gas chromatograph.

FIG. 16 illustrates another alternative embodiment of a multi-dimensional gas chromatograph 1600. Embodiments of gas chromatograph 1600 can be used in place of, or one or more of its components can be used to supplement, gas chromatograph (GC) 108 and/or detector 110 in gas analysis systems such as the ones shown in FIGS. 1A-1B and 5-9. Multi-dimensional chromatograph 1600 is in most respects similar to multi-dimensional chromatographs 1400 and 1500. The individual GCs 1602, 1604 and 1606 in chromatograph 1600 have at least the same features and characteristics as the individual GCs in chromatographs 1400 and 1500. The primary difference between chromatograph 1600 and chromatographs 1400 and 1500 is that in chromatograph 1600 certain elements of the Dean switch are integrally formed in the individual GCs. In the illustrated embodiment, Y-splitters Y1 is integrally formed in first GC 1602, along with fluid connections that allow GC 1602 to be coupled to the other GCs. Similarly, second GC 1604 has flow rate restrictor 1432 and Y-splitter Y2 formed therein, while third GC 1606 has third Y-splitter Y3 and flow rate restrictor 1440 formed therein.

Embodiments are disclosed of a new method of gas analyte (e.g., chemicals such as volatile organic compounds (VOCs)) spectrum sharpening and separation enhancement using multi-dimensional miniaturized gas chromatography column (GC) or micro-GC configuration. Unlike the traditional bulky GC system with slow and limited temperature control flexibility, the disclosed embodiments utilizes miniaturized GC/micro-GC columns, which can be cascaded with different coating materials for gas separation analysis. The micro-GCs are small in size (can be fabricated into micro-chip size if necessary) and thus can be promptly cooled down to sub-zero temperature with a simple small cooling device (e.g., thermoelectric cooler, TE cooler), which cannot be achieved using traditional bulky GC unless liquid nitrogen is used. With simple, fast, and direct micro-GC cooling, one can achieve direct column focusing effect, which sharpens the analyte spectrum and improves the column separation power. Furthermore, the disclosed embodiments can also include a cascade of multiple micro-GCs to form a heart-cutting gas chromatography configuration.

The disclosed embodiments are the first implementation of a direct fast GC cooling on micro-GC with simple cooling device, which allows the possibility of achieving spectrum sharpening without using liquid nitrogen. Meanwhile, they also improve the detection limit. As a result, the disclosed embodiments can be implemented as a portable gas analysis system and significantly improve the system resolution and detection limit.

The above description of illustrated embodiments of the invention, including what is described in the abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize. These modifications can be made to the invention in light of the above detailed description.

The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

The invention claimed is:

1. An apparatus comprising:
a first gas chromatograph including a fluid inlet, a fluid outlet, and a first temperature control; and
a controller coupled to the first temperature control, wherein the controller includes logic to apply a first temperature profile to the first temperature control to heat, cool, or both heat and cool the first gas chromatograph;
a second gas chromatograph having a fluid inlet, a fluid outlet, and a second temperature control;
a third gas chromatograph having a fluid inlet, a fluid outlet, and a third temperature control;
wherein the fluid outlet of the first gas chromatograph is coupled to the fluid inlets of the second and third gas chromatographs by a heart-cutting valve, wherein the second and third temperature controls are coupled to the controller, and wherein the controller includes logic to apply a second temperature profile to the second temperature control and a third temperature profile to the third temperature control to heat, cool, or both heat and cool the second and third gas chromatographs; and
wherein the heart-cutting valve comprises:
a first Y-splitter coupled to the fluid outlet of the first gas chromatograph,
a second Y-splitter coupled to the first Y-splitter, the fluid inlet of the second gas chromatograph, and a first secondary fluid connection, and
a third Y-splitter coupled to the first Y-splitter, the fluid inlet of the third gas chromatograph, and a second secondary fluid connection.

2. The apparatus of claim 1 wherein the first temperature profile comprises:
a first time period during which the temperature control cools the gas chromatograph from an initial temperature to a first temperature; and
a second time period during which the temperature control heats the gas chromatograph from the first temperature to a second temperature.

3. The apparatus of claim 2 wherein the initial temperature is substantially room temperature, the first temperature is lower than room temperature, and the second temperature is greater than room temperature.

4. The apparatus of claim 1, further comprising a three-way valve coupled to the first secondary fluid connection, the second secondary fluid connection, and a source of a secondary carrier fluid.

5. The apparatus of claim 1, further comprising a first flow restrictor in the first secondary fluid connection and a second flow restrictor in the second secondary fluid connection.

6. The apparatus of claim 1 wherein the heart-cutting valve further comprises a flow resistor coupled to the first secondary fluid connection between the first flow restrictor and the second Y-splitter and coupled to the second secondary fluid connection between the second flow restrictor and the third Y-splitter.

7. The apparatus of claim 1 wherein the heart-cutting valve is formed on a microchip.

8. A gas analysis system comprising:
a substrate;
a cascaded gas chromatograph having a fluid inlet and one or more fluid outlets and being mounted to the substrate, the cascaded gas chromatograph comprising:
a first gas chromatograph having a fluid inlet, a fluid outlet, and a first temperature control,
a second gas chromatograph having a fluid inlet, a fluid outlet, and a second temperature control, and
a third gas chromatograph having a fluid inlet, a fluid outlet, and a third temperature control;
one or more detector arrays having a fluid inlet and a fluid outlet and being mounted to the substrate, wherein the fluid inlet of each of the one or more detector arrays is fluidly coupled to a corresponding one of the one or more fluid outlets of the cascaded gas chromatograph;
a control circuit coupled to the cascaded gas chromatograph and to the detector array, wherein the control circuit includes logic to apply a first temperature profile to the first temperature control to heat, cool, or both heat and cool the first gas chromatograph, and wherein the control circuit can communicate with the gas chromatograph and with the one or more detector arrays; and
a readout circuit coupled to the one or more detector arrays and to the control circuit, wherein the readout circuit can communicate with the control circuit and the one or more detector arrays;
wherein the fluid outlet of the first gas chromatograph is coupled to the fluid inlets of the second and third gas chromatographs by a heart-cutting valve, wherein the second and third temperature controls are coupled to the control circuit, and wherein the control circuit includes logic to apply a second temperature profile to the second temperature control and a third temperature profile to the third temperature control to heat, cool, or both heat and cool the second and third gas chromatographs;
and wherein the heart-cutting valve comprises:
a first Y-splitter coupled to the fluid outlet of the first gas chromatograph;
a second Y-splitter coupled to the first Y-splitter, the fluid inlet of the second gas chromatograph, and a first secondary fluid connection; and
a third Y-splitter coupled to the first Y-splitter, the fluid inlet of the third gas chromatograph, and a second secondary fluid connection.

9. The gas analysis system of claim 8 wherein the first temperature profile comprises:

a first time period during which the temperature control cools the gas chromatograph from an initial temperature to a first temperature; and a second time period during which the temperature control heats the gas chromatograph from the first temperature to a second temperature.

10. The gas analysis system of claim 9 wherein the initial temperature is substantially room temperature, the first temperature is lower than room temperature, and the second temperature is greater than room temperature.

11. The gas analysis system of claim 8, further comprising a three-way valve coupled to the first secondary fluid connection, the second secondary fluid connection, and a source of a secondary carrier fluid.

12. The gas analysis system of claim 8, further comprising a pre-concentrator having a fluid inlet and a fluid outlet, wherein the pre-concentrator is mounted on the substrate and coupled to the control circuit, and wherein the fluid outlet of the pre-concentrator is coupled to the fluid inlet of the cascaded gas chromatograph.

13. The gas analysis system of claim 12, further comprising a filter and valve unit having a fluid inlet and a fluid outlet, wherein the filter and valve unit is mounted to the substrate and coupled to the control circuit, and wherein the fluid outlet of the filter and valve unit is coupled to the fluid inlet of the pre-concentrator.

14. The gas analysis system of claim 13, further comprising one or more pumps having a fluid inlet and a fluid outlet, wherein each pump is mounted on the substrate and coupled to the control circuit, and wherein the fluid inlet of each pump is coupled to the fluid outlet of a corresponding detector array.

15. The gas analysis system of claim 14, further comprising:

a three-way valve coupled in the fluid connection between the pre-concentrator and the gas chromatograph; and a fluid connection coupled to the three-way valve and to the fluid connections between the one more detector arrays and the corresponding pump.

16. The gas analysis system of claim 8 wherein the readout circuit includes thereon an analysis circuit and associated logic to analyze output signals received from the one or more detector arrays.

17. The gas analysis system of claim 8 wherein one or more detectors in each detector array is selective to a chemical that was unseparated or partially separated by the one or more gas chromatographs.

18. A gas analysis system comprising:

a substrate;

a cascaded gas chromatograph having a fluid inlet and one or more fluid outlets and being mounted to the substrate, the cascaded gas chromatograph comprising a first gas chromatograph having a first temperature control;

one or more detector arrays having a fluid inlet and a fluid outlet and being mounted to the substrate, wherein the fluid inlet of each of the one or more detector arrays is fluidly coupled to a corresponding one of the one or more fluid outlets of the cascaded gas chromatograph;

a control circuit coupled to the cascaded gas chromatograph and to the detector array, wherein the control circuit includes logic to apply a first temperature profile to the first temperature control to heat, cool, or both heat and cool the first gas chromatograph, and wherein the control circuit can communicate with the gas chromatograph and with the one or more detector arrays; and a readout circuit coupled to the one or more detector arrays and to the control circuit, wherein the readout circuit can communicate with the control circuit and the one or more detector arrays;

a pre-concentrator having a fluid inlet and a fluid outlet, wherein the pre-concentrator is mounted on the substrate and coupled to the control circuit, and wherein the fluid outlet of the pre-concentrator is coupled to the fluid inlet of the cascaded gas chromatograph;

a filter and valve unit having a fluid inlet and a fluid outlet, wherein the filter and valve unit is mounted to the substrate and coupled to the control circuit, and wherein the fluid outlet of the filter and valve unit is coupled to the fluid inlet of the pre-concentrator;

one or more pumps having a fluid inlet and a fluid outlet, wherein each pump is mounted on the substrate and coupled to the control circuit, and wherein the fluid inlet of each pump is coupled to the fluid outlet of a corresponding detector array;

a three-way valve coupled in the fluid connection between the pre-concentrator and the gas chromatograph; and a fluid connection coupled to the three-way valve and to the fluid connections between the one more detector arrays and the corresponding pump.

19. The gas analysis system of claim 18 wherein the first temperature profile comprises:

a first time period during which the temperature control cools the gas chromatograph from an initial temperature to a first temperature; and a second time period during which the temperature control heats the gas chromatograph from the first temperature to a second temperature.

20. The gas analysis system of claim 19 wherein the initial temperature is substantially room temperature, the first temperature is lower than room temperature, and the second temperature is greater than room temperature.

21. The gas analysis system of claim 18 wherein the readout circuit includes thereon an analysis circuit and associated logic to analyze output signals received from the one or more detector arrays.

22. The gas analysis system of claim 18 wherein one or more detectors in each detector array is selective to a chemical that was unseparated or partially separated by the one or more gas chromatographs.

* * * * *